United States Patent
Schussler et al.

(10) Patent No.: US 9,289,533 B2
(45) Date of Patent: Mar. 22, 2016

(54) COLLAGEN SCAFFOLD MODIFIED BY COVALENT GRAFTING OF ADHESION MOLECULES, ASSOCIATED METHODS AND USE THEREOF FOR CARDIOVASCULAR AND THORACIC CELL THERAPY AND CONTRACTILE TISSUE ENGINEERING

(75) Inventors: Olivier Schussler, Suresnes (FR); Robert Michelot, Anthony (FR)

(73) Assignee: Olivier Schussler, Suresnes (FR)

( * ) Notice: Subject to any disclaimer, the term of this patent is extended or adjusted under 35 U.S.C. 154(b) by 727 days.

(21) Appl. No.: 12/664,482

(22) PCT Filed: Jun. 10, 2008

(86) PCT No.: PCT/FR2008/000785
§ 371 (c)(1),
(2), (4) Date: Dec. 14, 2009

(87) PCT Pub. No.: WO2009/007531
PCT Pub. Date: Jan. 15, 2009

(65) Prior Publication Data
US 2010/0184183 A1 Jul. 22, 2010

(30) Foreign Application Priority Data
Jun. 13, 2007 (FR) .................................... 07 04209

(51) Int. Cl.
*C12N 11/02* (2006.01)
*A61L 27/56* (2006.01)
(Continued)

(52) U.S. Cl.
CPC ................ *A61L 27/56* (2013.01); *A61L 27/24* (2013.01); *A61L 31/044* (2013.01); *A61L 31/16* (2013.01); *A61L 2300/00* (2013.01);
(Continued)

(58) Field of Classification Search
None
See application file for complete search history.

(56) References Cited

U.S. PATENT DOCUMENTS 6,579,696 B1 * 6/2003 Shekhani et al. ............ 435/68.1
6,608,040 B1 * 8/2003 Lin et al. ..................... 514/54
(Continued)

FOREIGN PATENT DOCUMENTS

JP 2005229871 A 9/2005
JP 2006500975 A 1/2006
(Continued)

OTHER PUBLICATIONS

Myles J L et al, "Modification of the adhesive properties of collagen by covalent grafting with RGD peptides", Journal of Biomaterials Science. Polymer Edition 2000, pp. 69-86, vo I . 11, No. 1, XP009098120.
(Continued)

*Primary Examiner* — Robert Yamasaki
(74) *Attorney, Agent, or Firm* — Young & Thompson

(57) ABSTRACT

Materials and methods for improving the biological properties and electromechanical performance of collagen scaffolds used for cell transplantation, including the fixation of biocompatible reagents and adhesion molecules which control cell adhesion, apoptosis, survival and/or differentiation simultaneously. The grafting of adhesion molecules to collagen matrices renders same suitable for use in vascular and cardiothoracic surgery/medicine, as well as in cell therapy for the heart and in artificial heart muscle engineering. Also, a simple method for grafting and optimising the presentation of adhesion peptides or biological agents when the scaffold is made from collagen and/or contains accessible thiol, amine or carboxyl groups.

12 Claims, 10 Drawing Sheets

Figure 1:
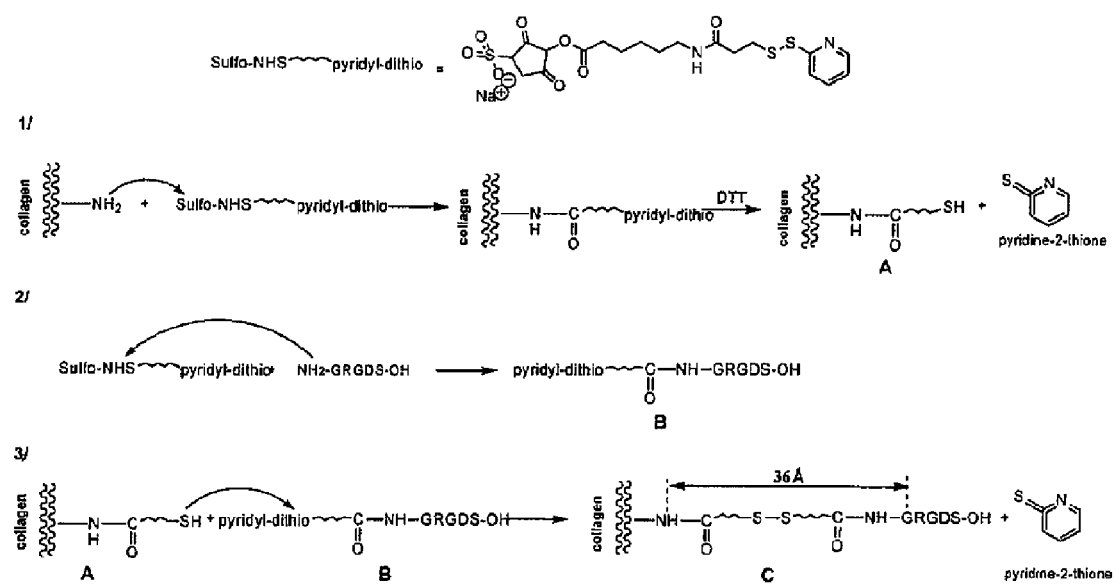

(51) Int. Cl.
*A61L 27/24* (2006.01)
*A61L 31/04* (2006.01)
*A61L 31/16* (2006.01)

(52) U.S. Cl.
CPC ......... *A61L 2300/80* (2013.01); *A61L 2400/06* (2013.01); *A61L 2430/20* (2013.01)

(56) References Cited

U.S. PATENT DOCUMENTS

| | | |
|---|---|---|
| 2005/0123582 A1 | 6/2005 | Sung et al. |
| 2007/0014874 A1* | 1/2007 | Matheny .................. 424/551 |
| 2007/0260299 A1 | 11/2007 | Gagnieu |

FOREIGN PATENT DOCUMENTS

| | | | |
|---|---|---|---|
| WO | WO 0240242 A1 * | 5/2002 | |
| WO | 2004012676 A2 | 2/2004 | |
| WO | 2006/037770 A | 4/2006 | |
| WO | 2007012051 A1 | 1/2007 | |

OTHER PUBLICATIONS

Chang Y et al, "Reconstruction of the right ventricular outflow tract with a bovine jugular vein graft fixed with a naturally occurring crosslinking agent (genipin) in a canine model",The Journal of Thoracic and Cardiovascular Surgery, Dec. 2001, pp. 1208-1218, vol. 122, No. 6, XP002475075.

Schussler Olivier et al, "RGD-coupling to collagen scaffold improves cardiomyocyte viability and contractility: New possibilities for cardiac tissue engineering" Circulation, Oct. 2007, p. 70, vol. 116, No. 16, Suppl. S, XP002475076.
International Search Report in Corresponding Application No. PCT/FR2008/ 000785, dated Feb. 19, 2009.
Christman et al., "Biomaterials for the Treatment of Myocardial Infarction", Journal of the American College of Cardiology, 2006, vol. 48, No. 5, pp. 908-913.
Fujita et al., "Accelerated de novo sarcomere assembly by electric pulse stimulation in C2C12 myotubes", Experimental Cell Research, 2007, vol. 313, pp. 1853-1865.
Sung et al., "Crosslinking of biological tissues using genipin and/or carbodiimide", National Science Council of Taiwan, Mar. 13, 2002, pp. 427-438.
Zimmermann et al., "Engineered heart tissue for regeneration of diseased hearts", Biomaterials, 2004, vol. 25, pp. 1639-1647.
Chang et al., "Reconstruction of the right ventricular outflow tract with a bovine jugular vein graft fixed with a naturally occuring crosslinking agent (genipin) in a canine model", The Journal of Thoracic and Cardiovascular Surgery, 2001, vol. 122, No. 6, pp. 1208-1218.
Ihara et al., "Development and Commercialization of Biomaterials Using Salmon Collagen", 2007, vol. 85, No. 3, pp. 126-131.
Engler et al., "Embryonic cardiomyocytes beat best on a matrix with heart-like elasticity: scar-like rigidity inhibits beating", Journal of Cell Science, 2008, vol. 121, No. 22, pp. 3794-3802.
Engler et al., "Myotubes differentiate optimaly on substrates with tissue-like stiffness: pathological implications for soft or stiff microenvironments", The Journal of Cell Biology, 2004, vol. 166, No. 6, pp. 877-887.

* cited by examiner

|  | T | TR | p |
|---|---|---|---|
| Basic angiogenesis (%) | 6.2 +/- 2.2 | 6.7 +/- 2.5 | ns |
| HUVEC cells | 7.0 +/- 3.2 | 7.9 +/- 3.0 | ns |
| Progenitor CD34 cells | 7.5 +/- 2.7 | 22.3 +/- 5.5 | p<0.05 |

Figure 8

COLLAGEN SCAFFOLD MODIFIED BY COVALENT GRAFTING OF ADHESION MOLECULES, ASSOCIATED METHODS AND USE THEREOF FOR CARDIOVASCULAR AND THORACIC CELL THERAPY AND CONTRACTILE TISSUE ENGINEERING

The present invention relates to collagen scaffolds characterized in that they are chemically modified by covalent grafting of adhesion molecules which facilitate the cell implantation, their survival and their differentiation. The collagen scaffold (hereunder referred to as "the support" or "the scaffold") may advantageously be used with contractile potential cells but other cell types may also be suitably used, or combined, such as angiogenic potential cells.

The present invention also relates to the covalent grafting method and to the uses of such substrates for tissue engineering, cell therapy or for modifying the collagen content of devices used in the thoracic and cardiovascular medical and surgical field.

The present invention relates to coated collagen substrates, especially for use in medicine, for tissue repair and regeneration.

Collagen takes part in many devices used in cell therapy, for tissue engineering and in the thoracic and cardiovascular medical and surgical field. These devices are intended to be implanted and cellularized and their functionality is optimized through a better cell-support interaction.

Collagen is improved through the covalent grafting of adhesion molecules which may thus interact in an optimal way with the membrane receptors of cells of interest (associated cells or which will colonize the support). Activating the receptors leads to a cascade of events which promote cell adhesion, cell growth, cell survival and which control apoptosis and cell differentiation.

The present invention also provides methods with a more general approach aiming at: 1) improving the fixation of the molecules such as adhesion molecules or biological agents (such as proteoglycans, growth factors or cytokines) to a support which would comprise thiol, amine or carboxyl accessible groups as is the case for collagen, 2) improving the biocompatibility of the collagen scaffold through cross-linking, by implementing chemical reactions that will not lead to toxic substances that might interfere with the cell growth in situ.

Nowadays tissue regeneration methods employ various techniques: a) the direct transplantation of free cells into the damaged environments b) tissue engineering techniques with the development of replacement tissue from cells injected into three-dimensional scaffolds. Producing cell therapy scaffolds is difficult because such supports enable the free diffusion of nutrients and oxygen, possess the mechanical properties but also the specific biological ligands to be able to interact with the associated cells of interest so as to promote their survival and their differentiation as well. Moreover, such a support has to favor the angiogenesis because it is not vascularized, as opposed to natural tissues. This support should be biocompatible and cause a little inflammatory response after implantation in vivo. Finally, this support should be clinically usable, be compatible with sanitary safety, thus excluding the use of a tumor extract. Until now such supports did not exist for cardiovascular and thoracic tissue engineering.

To this day, techniques for transplanting isolated cells suffer from causing a very substantial cell mortality and often a lack of differentiation of the transplanted cells. It is thus known from T. Yasuada and al.[1] that the use of fetal cardiac myocytes, of skeletal myoblasts and of marrow bone stem cells always encountered a mitigated success as regards the ability to repair damaged tissues and to improve the cardiac function. The lack of production of new myocardial fibers in sufficient numbers for a positive effect to be clinically transposed has been attributed to the substantial cell death occurring after the graft (approx. 90%) and to the inability for the grafted cell to differentiate and to get integrated to the myocardium[1,2]. The low survival rate of transplanted cells has been underlined in a plurality of works as being a possible explanation to the cell therapy failure wherein cells are injected in an isolated manner. This survival issue has been broadly illustrated by several groups which did show that modifying cells with survival genes could greatly improve their survival and their functionality after transplantation[3].

More recently, various groups did demonstrate the interest of associating cells with a three-dimensional support which would make it possible to recreate the native tissue environment with a cell transplantation into synthetic or biological supports as for example collagen[4-8]. The destruction of the native extracellular matrix (ECM) essentially composed of type I and type III collagen in the myocardium and its replacement with a less vascularized tissue having altered mechanical properties (less compliant), which, in addition, due to a change in its composition, does not allow an optimal interaction anymore, could explain the relatively poor results of the free cell transplantation. The presence of a collagen matrix thus significantly improves the muscular tissue regeneration[9]. Injecting cells by the endovascular route is being assessed as regards the myocardial regeneration and could be rather interesting[10]. Injecting collagen microspheres has also been performed by portal vascular route prior to injecting cells of the hepatic cell type into the same vessels or into the vascularized regions or into the draining regions thereof so as to support their survival[11]. Collagen-containing injection gels or hydrogels may also be obtained by associating collagen microparticles with synthetic particles such as carbon nanotubes[12] or with natural polymers such as chitosan.

The identification of the microenvironment characteristics affecting the cell phenotype and its function within the collagen matrix provides the suitable conditions for the artificial myocardial tissue engineering in medical applications[13,14]. In tissues, such 3D-environment is formed by the extracellular matrix which is made of proteins. Collagen is one of the main structural proteins of this environment[15]. Cells interact with this environment by means of surface receptors called "integrins" which recognize elementary sequences, most often peptide sequences, and which are present on the ECM proteins[13,16]. There are transmembrane heterodimeric receptors formed by the association of an alpha chain with a beta chain. The activation of such receptors will depend upon the presence of the ligand on ECM but also upon the presentation of this ligand and the combinations of the various receptors. The activation of the molecule receptor or that of the adhesion peptide sequence receptor, i.e. integrin receptor, is responsible for intracellular event cascades together with some rearrangements of the cell cytoskeleton, the activation of various signaling pathways which control the cell survival[17,18], shape[19], proliferation, apoptosis[17], and differentiation[20][21]. For this activation optimally to occur, not only the ligand should be present on the ECM, but it should also be suitably presented to interact with the integrin receptor[22-24]. On the other hand, there is at the time of receptor activation a physical coupling which occurs between the cell cytoskeleton and the cytoplasmic part of the integrin receptor[25]. An actual bridge is thus created between the ECM, the ligand, the integrin receptor and the cytoskeleton. By means of these connections, forces are exerted by the cell onto the ECM and the development of these forces is necessary for the optimal activation of these receptors[14,26,27]. Therefore, for enabling the development of such forces, the ligand should be firmly fixed, and also the ECM should have some resistance while still remaining its relatively plasticity[14]. In the event of contractile cells such as cardiac myocytes, the differentiation is exclusively obtained with moderately rigid substrates[28]. Endothelial cells do differentiate and form capillaries or tubular structures on flexible substrates whereas they tend to spread and to proliferate[29] in a greater extent on more rigid substrates.

To obtain contractile tissues, various types of tissues have been developed by combining contractile cells with synthetic or biological supports (alginate, collagen I, fibrin)[4-8,30]. Up to now, no in vitro contractility has been reported in synthetic matrices or in matrices resulting from nanotechnologies using oligopeptide polymerization (cf. PURAMETRIX®[31,32]. The best results as regards the in vitro contractility were obtained with collagen matrices. Such collagen matrices are most often resulted from the physical cross-linking of collagen fibers according to the so called dehydrothermal treatment (DHT)[33,34]. This collagen cross-linking method however remains considered as moderate when compared to other chemical cross-linking methods. The advantage of such collagen matrices is their porosity which facilitates the cell inserting as well as the nutrient and oxygen diffusion[35]. However the cell survival in this type of support is still low and the differentiation remains partial, with especially a lack of terminal differentiation for cardiac myocytes[5] and for endothelial cells[36-39]. Spontaneous contractions in this type of matrix are unusual[40,41], and when present they are anarchical in nature[42,43]. Arrhythmias are frequent. In an effort to improve these parameters, some authors suggested to use a protidic extract of a MATRIGEL™ type basal membrane associated with a physical stimulus such as a mechanical stress[44] or a chronic electrostimulation[40,41] and a very high xenogeneic serum content in the culture medium. MATRIGEL™ is an extracellular protein extract derived from the basal membrane of a kidney tumor (cf "Engel Brecht Swarm tumours"). MATRIGEL™ may not be employed alone because of its insufficient collapse resistance and it should be associated with a more rigid synthetic or biological support. In the present state of our knowledge, the use of contractile tissues obtained using MATRIGEL™ is not allowed for human clinical medicine due to the origin of such compound. Moreover, the presence of MATRIGEL™ may generate a number of side effects. This gel restraints the free diffusion of nutrients and it becomes then necessary to use continuous infusion systems such as bioreactors[41]. The diffusion deficiencies limit the thickness of the expected tissue and make it unsuitable for replacing a cardiac muscle.

Promising results have been obtained in vivo in animals[4,5,7] with collagen scaffolds that were cellularized with contractile cells still in presence of MATRIGEL[45]. These preparations in vivo may continue to beat for a couple of weeks in different sites[46,47] and even may improve the cardiac systolic function after application onto the cardiac muscle[45]. A spontaneous synchronization between these supports and the myocardium of the recipient animal was even observed in some situations.

In spite of these preliminary results, collagen matrices after implantation in vivo induce an intense inflammatory response that rapidly causes the degradation of collagen matrix[47]. Such accelerated matrix degradation subsequent to the strong inflammatory response is responsible for the local release of great amounts of enzymes, free radicals and various degradation products which may also compromise the survival of the cells associated with those supports. The collagen degradation products themselves have been reported as being toxic in nature, especially for contractile cells[48]. Moreover, the mechanical properties of the supports are impaired by this degradation even before the associated cells could form their own matrice[49]. The cell survival in the 3D-supports thus remains generally low[50]. It is even lower in collagen scaffolds and the differentiation in vivo of contractile cells in collagen scaffolds is still incomplete. Moreover, the poor angiogenesis in the implant limits the functionality thereof. To improve the situation MATRIGEL™ was indispensable. The use of Matrigel combined with synthetic matrices in order to make an artificial myocardium was suggested (cf. Levenberg and al. US patent 2005/0,031,598). However Levenberg and al. underlined that MATRIGEL physical properties are not stable in vivo and that cells, after their first differentiation, do rapidly de-differentiate in this type of gel. Moreover, the limitation to the MATRIGEL™ use for such applications is explained by the fact that MATRIGEL™ is above all a tumor extract and therefore cannot be used in human medicine. On the other hand, MATRIGEL™ induces a very strong inflammatory response in vivo which makes it necessary to treat the animal with immunosuppressants[45,47]. In addition, MATRIGEL™ induces the formation of a secondary cicatricial and poorly vascularized fibrosis which on the long run compromises the cell survival.

The degradation of the collagen matrices is generally diminished by methods for cross-linking collagen fibers. The DHT-mediated cross-linking is a physical cross-linking conventional method[33,51]. Thus, some hemostatics for clinical use are obtained by using the DHT method such as the ULTRAFOAM® matrix (Bard). Initial collagen is soluble in a 0.5% w/w collagen solution in acetic acid 0.05 M, pH 3.5. The preparation is cryodried in a controlled manner so as to obtain sponges. The pore size and distribution for the most part depends on the freezing rate (0.25-1° C/min.) and on the final freezing temperature (from −90° C. to −5° C.)[52]. This sponge is then submitted to a DHT-cross-linking (105° C. for 16 hr at a pressure of less than 100 mTorr) for introducing covalent bonds between the collagen chains without denaturing its gelatin[53 54]. While these matrices are compatible in vitro with the development of a myocardial tissue (thanks to its architecture, its resistance, its mechanical properties, its pore size that is compatible with the nutrient diffusion)[40,55], this collagen matrix obtained through DHT induces an intense inflammatory response after its implantation in muscles (spinal skeletal muscle for example) leading to its degradation within a couple of weeks.

It should therefore be envisaged to use or to combine other collagen cross-linking methods. To restrain such degradation, collagen may be associated with synthetic polymers[56] or with organic or inorganic compounds such as silk for example[49].

Very recently, a transglutaminase-mediated enzymatic cross-linking has been proposed[57]. Collagen cross-linking may be obtained by cells and by their natural products. Such endogenous cross-linking may be increased by using ascorbic acid or riboses. Cross-linking may be obtained through muscle cells which produce a lysyloxidase type enzyme performing a cross-linking between free amine groups of lysine residues and hydroxylysine residues of collagen. An alternative approach consists in cross-linking collagen fibers by means of chemical treatments such as, for example, a cross-linking[58] using glutaraldehyde, diphenylphosphorylazide (DPPA), carbodiimides[59], etc.

The most efficient method for cross-linking collagen is still the glutaraldehyde-mediated chemical cross-linking[51,58].

However glutaraldehyde may auto-polymerize, then slowly depolymerize within the biological preparation and, thus, release free glutaraldehyde which is toxic to the cell and therefore not compatible with cell therapy.

Thus, although it was suggested to make heart tissue with synthetic supports (U.S. Patents No. 2005/0,031,598, 2004/0,242,469), there are not today synthetic or biological three-dimensional supports for use in humans and in which a contractility has been demonstrated in presence of contractile cells[60], thus explaining the object of the invention.

Moreover, in addition to collagen-based supports, other fibrin- or fibrinogen-based biological supports are being developed and fibrin supports have been suggested for injecting cells into the myocardium[61-64]. Fibrinogen is soluble and under the action of thrombin and calcium, fibrinogen is converted to fibrin which precipitates. The properties of this gel may be monitored through the thrombin and fibrinogen[65] concentration. The physical properties of the fibrin fibers as regards extensibility and adaptability under constraints are excellent[66].

Fibrin is a biomaterial which is used for cell therapy and tissue engineering. Fibrin has been proposed for delivering cells to synthetic supports or for preparing heart tissues[67], for injecting cells into the myocardium[68] (U.S. patent 2005/02,761,631), for preparing heart valves[69], cardiac stents[70], for healing bronchial tissue[71], for making vascular ducts[71].

It has been demonstrated in vitro that during gelling, various growth factors or adhesion peptides such as RGD peptides could be added to the support[72]. Amongst those factors, the presence of a RGD peptide improves the angiogenesis within the support although fibrin already contains the RGD moiety[73]. It should be noted nevertheless that in these experiments, the RGD is not covalently fixed to the support and that fibrin gels, in addition, tend to get compact as time goes, their mechanical properties being impaired and the support not allowing angiogenesis to develop anymore[74]. Using this type of gel with stem cells also create a number of problems because if the fibrinogen concentration is too low, the gel does liquefy and get lost within a couple of weeks. If the collagen concentration is too high, stem cells do not differentiate anymore in this type of support[75]. It should be also noted that it has also been proposed to associate fibrinogen with other components[76] and that hydrogels with collagen and fibrin also have been developed[77]. For all the previously mentioned reasons, we suggests in the present invention to change the collagen component or fibrinogen or fibrin associated with the support using adhesion molecules which are covalently bound.

Amongst the adhesion molecules, the RGD moiety (Arg-Gly-Asp) is a ligand recognized by a number of integrin receptors, especially those present on contractile cells or their progenitors and endothelial cells. There are many other adhesion peptide ligands. This ligand is normally present on collagen but in a form that is not accessible to cells if collagen is not denatured ("cryptic expression"). Modifying the collagen scaffold with RGD molecules has been proposed in various applications[22] such as bone regeneration and for making dermal tissues[51]. In the thoracic and cardiovascular field, the covalent association of collagen with adhesion moieties (or adhesion units) such as RGD peptides has never been proposed for tissue engineering and cell therapy. When the RGD moiety was mentioned, the previous studies described the harmful effect of RGD as regards to contractility, myocardial function, rhythmicity and the developed forces. The fact that the RGD moiety is not bound could explain the harmful effect of RGD onto the muscular contraction reported by Sarin and al.[78] and the unit internalization[79], as well the results reported by S Y. Boateng and al.[80]. As is suggested in the present invention, these negative results are probably due to the inappropriate use of the RGD peptide and to the lack of covalent bond for the peptide used to the support in all these different works. This explains the moiety internalization in the study of S. Balasubramanian and al.[79]. Using a RGD moiety for cardiac cell therapy was proposed (U.S. patent 2005/0,271,631) but RGD was associated with fibrin gels and not with collagen, the RGD was not covalently bound and the other adhesion molecules were not mentioned. In medical and surgical devices for use in the thoracic and cardiovascular field, it has been proposed to associate the RGD moiety with the metal component of a coronary stent so as to promote the adhesion of the circulating endothelial cells and make the stent less thrombogenic. The cyclic RGD has been recently associated with the matrix component (synthetic polymer) of a metal stent (silver) to reduce premature restenosis by promoting the adhesion of the circulating progenitors for endothelial cells[81]. Fixing adhesion peptides to supports that would be synthetic rather than collagenic in nature has been envisaged for heart tissue engineering. The fact remains that to this day no contractility in vitro or in vivo could be demonstrated in this type of synthetic support[60].

Until now, no contractile activity could be demonstrated in vitro and in vivo in synthetic type supports. Only collagen scaffolds enabled the development of contractility. The terminal differentiation of cardiac myocytes in vitro could be only obtained in the presence of a tumor extract of the MATRIGEL type, what explains the interest for collagen scaffolds modified according to the present invention.

Various modes were proposed for grafting adhesion peptides to collagen. Generally, a peptide reactive group does react with an amine group present on collagen, either on the polypeptide chain terminal ends, or on lysine side chains. For example the C-terminal end is converted to acyl azide. The binding of the peptide to collagen then occurs through an amide bond. This method results in the formation of numerous by-products, it is not selective and does not allow to use spacers which maintain the grafted peptide sequence that may bind to the integrin receptor reasonably spaced apart from the protein collagen. An alternative approach consists in modifying the peptide with an isothiocyanate group and in making this group react with the primary amine so as to obtain a thioamide type bond. The latter method has been proposed by Myles and al.[82] who suggested to fix to collagen an adhesion peptide such as RGD before fibrinogenesis occurs by using a water-soluble PIERCE™ heterobifunctional coupling agent (Sulfo-LC-SPDP) which enables to bind a thiol group-containing peptide to a primary amine group of collagen. The coupling agent linear size is of about 16 angstroms.

The technique described by J L. Myles and al.[82] is limited to the use of adhesion peptide sequences bound to a thiol-containing residue, which generally requires to modify the peptide by coupling it with a cysteine molecule. The peptide modification may change the interaction of the peptide with its receptor. The authors suggested to perform the coupling of the peptide with a liquid phase collagen before fibrinogenesis occurs. To prevent a spontaneous fibrinogenesis from occurring, reactions should be conducted under acidic pH conditions. But the coupling of the peptide with collagen is facilitated in a basic or a neutral medium. In addition, the purification of the reaction products carried out in a homogeneous phase is difficult and the by-product separation makes it necessary to use several chromatography purification steps. This difficulty may be alleviate if the reaction is carried out in a heterogeneous phase, for example on collagen that has been made insoluble by cross-linking pre-treatments. Lastly, the technique of Myles J L and al.[82] does not allow to monitor the coupling reaction progress and leaves aside available amino groups that might create peptide sequences duplication reactions. In addition thereto, the mutual spacing of adhesion peptides obtained according to this method is at most of 16 angstroms, which is substantially insufficient to present adhesion peptides in an optimal way (30-40 angstrom)[23,24]. We suggest in the present invention a solution to this problem.

It is an object of the present invention to provide a three-dimensional biological natural environment optimized for cell therapy or tissue engineering, or to improve devices for medical or surgical applications in the thoracic and/or cardiovascular fields. The present invention relates to the production of a support or a scaffold or a three-dimensional scaffold, where these terms may be used indifferently. This support contains collagen or fibrin or fibrinogen or a combination of these components which, besides, are modified through the addition or the covalent binding of adhesion molecules associated or not with bioactive agents which are not necessarily available or accessible on the original scaffold. These modified three-dimensional supports may be seeded and/or colonized with cells that are able to develop their physiological potentialities.

The three-dimensional scaffold contains cross-linked or not cross-linked components. The three-dimensional scaffold may be formed prior to or secondarily after the implantation following the polymerization of some of its components. The three-dimensional scaffold may be injected in some cases. This injection may be carried out for example in a vessel, in a bronchial lumen, in a tissue, in a space or a cavity, in another support, in a medical device used in cardiovascular and thoracic therapy, or in combinations thereof. The injection may be carried out in vitro and/or in vivo. The three-dimensional scaffold may result from the polymerization of some components that would occur spontaneously after implantation or after photoactivation, irradiation like ultraviolet irradiation, gamma irradiation, electric current, magnetic interaction, ionic interaction, chemical interaction, temperature, ultrasounds, salt, hydrophobic/hydrophilic coils, van der Waals forces, aromatic binding $-\pi$ metal-ligand, pH, concentration, redox, phosphorylation, stack, mechanical forces, electromagnetic forces or gravitational forces. Such polymerization or cross-linking may result from a chemical reaction with known cross-linking agents and derivatives and/or analogues thereof, combinations thereof, genipin, nordihydroguaiaretic acid aglycone, geniposidic acid, epoxide compounds, dialdehyde starch, glutaraldehyde, formaldehyde, dimethyl suberimidate, carbodiimides, succinimidyls, diisocyanates, acyl azide, glyceraldehyde, cyanamide, diimides, dimethyl adipimidate, ruterine, nordihydroguaiaretic acid, enzymatic conversion, thrombin, dehydrothermal treatment, endogenous cross-linking through cells and their normal biochemical products (such as cell-mediated lysine oxydase) or combinations of some of these methods.

The three-dimensional scaffold is fully or partially biodegradable, or non biodegradable.

The three-dimensional scaffold is formed in a liquid phase which, once delivered, after activation or without activation, may be converted to a solid phase (for example a solution, a paste, a gel, a suspended colloid, plasma).

The three-dimensional scaffold may be composed of a hydrogel made of hydrophobic and hydrophilic amino acids able to spontaneously combine together to form macroscopic structures.

The three-dimensional scaffold may be a gel or a surfactant

The three-dimensional scaffold wherein said scaffold is a surfactant is an "intelligent agent", that is to say a biological material composed of spontaneously assembled structures on a large scale underlying on local interactions at the molecular level.

In the three-dimensional scaffold, the 3D-construction may be obtained by stacking cultures obtained by different 2D-scaffolds. The cell adhesion to such 2D-support may be adjustable. These 2D-supports may include collagen/fibrin/fibrinogen modified through adhesion molecule fixation.

Many 3D-scaffolds, with various natures, may also be stacked in a sequential way or not.

The three-dimensional scaffold may form a cell matrix wherein the artificial tissue construction contains biomaterials having selected shapes so as to facilitate the structure assembling in the form of micro or nano-structures (for example micro or nano tubes, nanoparticles, micro- or nanopores. Microparticles or nanoparticles are made of silicon, poly-(lactic acid)-copolymer-glycolic lactic acid mixture, cyclodextrine, liposome conjugated or not to the nanoparticles quantum dot, magnetite, filaments, structural analogues to form the external interface, peptide analogues, β-/or-α structures forming filaments or tubes of sponge, powder, duct, sphere, microsphere, film, micro- or nanofibrils, lipid membranes, fiber, meshes, matrices, patches, tissue leaves, interlining or combinations thereof.

The various types of support may be associated with each other.

The three-dimensional scaffold comprises collagen composed of collagen (I, II, III, IV, V, VI, VII, XI types and others), or of the association of various species. The word "collagen" also encompasses insoluble collagen, soluble collagen, atelocollagen prepared by removing telopeptides at the ends of the collagen molecules by using a protease other than collagenase. The three-dimensional collagen scaffold may also be a normal tissue of autologous, homologous or heterologous origin. This tissue may be decellularized or not, physically and/or enzymatically (for example with collagenase) and/or chemically modified or associated. Collagen may be purified from a collagen-containing tissue: autologous, homologous or heterologous such as (ureter, pericardium, submucous such as pig intestine submucous "SIS"[83,84], blood vessel, tendon, fascia, decellularized or non decellularized, aponeurosis, membrane of the amniotic type, dura mater, heart valve, etc.). It could also be collagen synthetic copies such as polymer fibers or fibril-forming peptides. Collagen may be chemically modified and the product obtained by succinylation or esterification or formation of carboxyamides, or desamination of the hereabove described collagens, a mixture of collagen with synthetic polymers such as poly-lactic acid) (PGA) and/or poly (DL-lactide-Co-glycolide) (PLGA) and/or poly (DL-lactide-Co-caprolactone) (PCL), a collagen derivative such as gelatin, a polypeptide obtained by hydrolyzing collagen, heat denatured collagen. Collagen-bound synthetic polymers may be selected from polylactic acid (PLA), polyglycolic acid (PGA), poly (L-lactic) acid (PLLA), PLGA, poly (anhydrides) (PA), polycarbonate (PC) hydroxy-acids, poly ortho-esters (POE), propylfumarates (PPF), polysaccharides, polylactone (PL), polycaprolactones, polyamides, polyamino acids, polyacetals, polyphosphazenes (PPZ), biodegradable polycyanoacrylates, biodegradable polyurethanes (central unit), polysaccharides, polypyrrole, polyanilines, polythiophene, polystyrene, polyester (PE), non-biodegradable polyurethanes, polyureas, poly (ethylene-terephthalate) (PET), poly (ethylene vinyl acetate), polypropylene, polymethacrylate, polyethylene, polycarbonates, polyethylene oxide, polyvinyl alcohol (PVA), fuseau-tex (polytetrafluoroethylene), dacron (polyethylene terephthalate), polytetrafluoroethylene (PTFE), polyethylene glycol (PEG), copolymers described hereabove, with one of the previously mentioned additives, and mixtures of one or more of these polymers, copolymers and additives, and associations of synthetic derivatives with biological products.

Collagen can be just a component of the 3D-scaffold, the said 3D-scaffold may comprise synthetic, inorganic substances (such as glass, $Si/SiO_2$, titanium/titanium dioxide, or, chromium, cobalt, diamond, platinum and hydroxyapatite, nitinol, steel, silica, streptavidin-biotine, a synthetic protein such as latex, nylon, catguth, cotton-wool, cloth, polyester, silk, plastic, ceramics, alloys, textile, avidin, streptavidin, caprolactone-Co-L-lactide copolymer sponge reinforced with poly-L-lactide, made in a knitted fabric of hyaluronic acid (PCLA), starch and any combination thereof), organic biological materials (such as proteoglycans, glycoproteins, glycoaminoglycans, alginate, agarose, hyaluronic acid, agar, chitosan, the fibrinogen/fibrin combination, carboxymethyl chitosan and their mixtures, gelatin, sucrose octasulfate, dextrane, cellulose, methylcellulose, sepharose, Sephadex-like protein (such as latex) or their combinations. The three-dimensional collagen scaffold may be the "collagen" contained in the medical device for use in cardiovascular and thoracic medicine and surgery as for example: heart valves (for example valves produced from autologous cells including cordage, papillary muscle, etc.), artificial hearts, valvular rings, tube valves, collagenic contents of coronary stents (of the "drug eluted stent", "cellularized stent", "biodegradable stent" type), hemocompatibility membranes, glues, (partially, totally or not) biodegradable myocardial contention devices which may be cellularized or not and/or associated (physically or not) with another support which in turn may be cellularized, patches, biological heart assistance to help contractility or regeneration for example. A myocardial replacement, a contention system to treat myocardial conditions or a pathological myocardium. A vascular duct that is spontaneously contractile or becomes contractile upon electrical stimulation for example, a biological pacemaker, a cell injection support, a replacement matrix or support, a cell therapy-associated support, a vascular prosthesis, vascular duct (including coronary graft), endoprostheses, regeneration materials or materials dedicated to tissue repair or replacement, to healing, for preventing dehiscence, promoting tightness, tracheal and or bronchial replacement prosthesis/tissue, bronchial endoprosthesis, bronchial or tracheal duct, "bronchial coil", "bronchial by-pass", lung tissue, device for releasing agents, collagen 3D-support associated with a medical or a surgical device, etc.

The scaffold may also be based on low or high molecular weight fibrin. The various collagen modifications may apply to fibrin. Fibrin and fibrinogen may be used interchangeably. The "collagen" "fibrinogens"/"fibrin" various forms may be associated with each other.

It is an object of the present invention to provide a three-dimensional biological natural environment, optimized for cell transplantation in the myocardium for example through the modification of collagen by adhesion peptides. Collagen is a natural molecule which already comprises some cell ligands. However cells, depending on their cell type, their differentiation level and their activation state express such and such adhesion receptor, such as integrin receptor for example. The expression diversity of these receptors enables the cell to interact very specifically with its environment and for a given environment to allow the growth of such and such cell type, or not.

Adhesion molecules may bind chemically to fibrinogen or fibrin and/or be comprised in the preparation-associated collagen component in the case of collagen gel and fibrin for example.

Adhesion molecules include polynucleotides, adhesion peptides including peptides, polypeptides, proteins or molecules that are able to bind, with a high affinity, to cell receptors which promote cell adhesion such as integrin receptors and according to the current bibliographic data. Adhesion peptides may be formed of natural amino acids of the natural type, or not, and/or analogues thereof. One or more amino acids the adhesion peptide may be substituted. Adhesion peptides include peptides, polypeptides or proteins or molecules (of natural origin or not) comprising the initial adhesion sequence. The words polypeptide, peptide and protein may be used in an interchangeable manner. This further comprises the addition of a chemical entity such as a carbohydrate group, a phosphate group, a farnesyl group, an isofarnesyl group, a fatty acid group, a binding promoter for conjugation, functionalization or any other organic or inorganic molecular modification or association including polyethylene glycol (PEG) or any other synthetic molecule. These modifications may also include cyclization of the adhesion sequence-containing peptide. Several adhesion peptides may be associated with each other and the peptide may relate to a single peptide or to a plurality of peptides Adhesion molecules or peptides may be modified and also belong to the same molecule or to a molecule acting as an intermediate for binding to the support.

Further included in the peptide are those adhesion peptides which aim at interacting with the adhesion receptor itself, with the co-receptors (not necessarily taking part to the adhesion). Binding to these co-receptors modifies the receptor adhesion and/or the receptor activation and/or the receptor transduction.

According to the present invention, the adhesion peptide could be advantageously the RGD peptide (arginine (R)-glycine (G)-aspartic acid (D)), a moiety that recognizes integrin on fibronectin described by Pierschbacher and al. (("linear RGD") (Pierschbacher M D. and al. 1984)[85]), or on vitronectin as described by Plaff M. and al. (("cyclic RGD") (Plaff M. and al. 1994)[86]). The "RGD moiety" also includes all the peptide ligands which will interact with one of the integrin receptors $\alpha_V\beta1$, $\alpha_V\beta3$, $\alpha_V\beta5$, $\alpha_V\beta6$, $\alpha_V\beta8$, $\alpha_{IIb}\beta3$, $\alpha_4\beta1$, $\alpha_4\beta_7$, $\alpha_5\beta_1$, $\alpha_8\beta_1$. Other adhesion peptides such as PHSRN peptides or proteoglycan mandatory domain of the extracellular matrix (heparin mandatory domains) based on X-B-B-X-B-X or X-B-B-B-X-X-B-X, B-B-X-B order models, wherein B is a basic amino acid and X is a hydroxy-amino acid, YIGSR (Iwamoto and al. 1987)[87] and IKVAV (-Ile-Lys-Val-Ala-Val-) (Tashiro and al. 1989)[88] RYVVLPR or RNI-AEIIKDI (Liesi P. and al. 1989)[89] from laminin, REDV (Massia S P and al. 1992)[90], PHSRN (-Pro-His-Ser-Arg-Asn) (Aota S. and al. 1994) or KNEED (Altroff H. and al 2001, Wong J Y and al. 2002)[91,92] or EILDV from fibronectin, proteoglycan mandatory domain of adhesion proteins such as KRSR (Dee K C and al. 1998; Rezania A. and al. 1999)[93,94] or FHRRIKA (Rezania A. and al. 1999)[95], elastin VAPG and KQAGDV sequences (Mann and West and al. 2002)[96], GFOGER from type I collagen (Emsley J. and al. 2000)[97], DEGA.

In a particular case of the invention, the ligand contains the RGD moiety present on the ECM proteins such as fibronectin or vitronectin but very numerous other ligands may be associated in the same way (for example peptide sequences derived from laminin, etc.) including those already present on collagen.

The present invention also provides a simple method, based upon a scaffold made of collagen, for all or part thereof, and comprising available functional groups, such as thiol or amine or carboxyl groups, for binding to adhesion molecules or molecules of interest or for releasing them in situ in a controlled manner. This method tends to improve the presentation of these molecules or of the biological agents (such as proteoglycans, growth factors or cytokines) towards membrane receptors of cells that can be homed in the modified collagen matrix.

In a particular use of the invention, the heterobifunctional coupling agent is sulfo-LC-SPDP.

The present invention is characterized by an improved spatial presentation of the peptide or of the growth factor, a reduction of the number of by-reactions or unwanted inter and/or intramolecular coupling, which improve the coupling overall efficiency while enabling to monitor each step of the method.

The technique used employs a single heterobifunctional reactant that is on the one hand bound to the adhesion peptide and to the other hand bound to the collagen support. The functionalization of the collagen support enables moreover to present the adhesion peptide to the substrate thereof at a distance of 36 angstrom, which is a distance considered as optimal for presenting adhesion peptides (ranging from 30 to 40 angstrom)[23,24]. The reaction enables to couple in an unidirectional way the peptide onto the active site of the support without duplicating the peptide. All the reaction intermediate steps can be controlled by simple spectrophotometry analysis of the medium. If the coupling of the molecule is conducted on a solid support, there is no need to perform any chromatography to remove the intermediate products which may be removed by simple washing. Moreover, the reaction may be carried out at neutral or alkaline pH, i.e. under most favorable conditions for conjugation. The molecule may comprise masking groups allowing successive reactions with the substrate and the ligands. Binding methods relate to molecules that do react with amino acid side chains (for example amine or thiol or alcohol or aldehyde or amide or acid groups or combinations thereof) in the substrates (for example the 3D-scaffold and the selected RGD-peptides). The method applies if the binding did occur prior to or after the collagen fibrinogenesis. This method also applies to any method for coupling collagen amine groups by using a heterobifunctional coupling agent also comprising a masked thiol group enabling the separate activation of the peptide and that of the collagen. These chemical bindings may also be formed irreversibly by other means such as ionizing radiations, free radical initiation or other molecular rearrangement. A maleimide residue may be used rather than a pyridyl disulphide group. The present invention also proposes a method for binding the RGD moiety as a sulfur derivative to a metallized scaffold, in which case the metal would be coated with a thin metal layer having a strong affinity towards the sulfur atoms of the RGD peptide functionalized for the coupling. In addition the covalent bond of the adhesion molecule to the support or to the agent fixed onto this support may be subsequently cleaved through chemical, enzymatic, thermal, mechanical reactions or combinations thereof.

The present invention describes methods for increasing the biocompatibility of collagen scaffolds by using non toxic chemical reactants enabling the cross-linking of the support, the fixation of the molecules of interest and the in situ cell growth which is promoted by the presence of adhesion molecules such as adhesion peptides or previously mentioned factors.

Up to now, the collagen most efficient chemical cross-linking had been obtained with glutaraldehyde. Glutaraldehyde may polymerize and subsequently hydrolyze, thus releasing a cytotoxic free glutaraldehyde. Such a scaffold therefore cannot be used for tissue engineering applications.

A fixing mode thus consists in providing an irreversible fixation of glutaraldehyde by neutralizing residual aldehyde groups through irreversible cross-linking of a glycosaminoglycan such as heparin or heparin sulfate. In the first approach, the tissue is fixed using glutaraldehyde and the aldehyde free groups are irreversibly neutralized by using glycosaminoglycan (GAG) such as heparin/heparin sulfate, chondroitin sulfate, dermatane sulfate. GAG are known as regulating the matrix hydration degree but they also act as ligands for many growth factors. Lee and al. reported a method for limiting the reactive aldehyde groups after fixation with glutaraldehyde by blocking with amino polyethylene oxysulfonate, (cf. $NH_2$-PEO-$SO_3$ (cf. Lee and al. (2001))[98] or with heparin. Dove J S (U.S. patent 2006/0,217,805) proposed to fix the tissue with glutaraldehyde, then to treat said tissue with a reducing agent that could reduce glutaraldehyde, probably imines and carboxyl groups on fixed tissues. However the method used for fixing a tissue can be hardly transposed to a collagen scaffold that is in particular more sensitive. It seems to be more appropriate to use less drastic reducing agents to reduce the imine groups resulting from the reaction of the amine groups with glutaraldehyde.

In order to improve the compatibility, an alternative approach would aim at using cross-linking agents different from glutaraldehyde. It is known from Y. Chang and al. (2002); H C Liang (2004); C C Tsai and al. (2001)[99,100] (U.S. patent 2005/0,013,802) to propose genipin for cross-linking native or de-cellularized tissues. By contrast using genipin has not been proposed as an agent for fixing collagen scaffolds, re-created from collagen fibers and intended to be cellularized. The only publications, as regards the use of genipin in the cardiovascular field, relate to the degradation control of the collagen component in medical devices such as "drug eluted stent" (U.S. Patent 2005/0,123,582). It does not relate to cellularized stents in this situation, as the "drug" component aims at controlling the cell proliferation by its toxicity. In the present invention the applicant suggests to use genipin associated, or not, with other physical treatments such as UV, beam ionizing radiation, dehydration and thermal treatment (dehydrothermal crosslinking (DHT) K S Weadock and al (1996)[33] for stabilizing the collagen artificial matrix (collagen, gelatin or chitosan), for tissue engineering procedures after or prior to associating with adhesion peptides such as RGD.

The present invention is different from the U.S. patent of Mooney and al. U.S. Pat. No. 6,642,363 (2003) in that it relates to the production of an artificial tissue for cardiovascular applications comprising essentially myocytes seeded into a biodegradable collagen matrix, whereas the mentioned authors described how to make a tissue from polyalginate chains.

The present invention is different from the U.S. patent of Barerra and al. U.S. Pat. No. 5,399,665 (1995) which uses functionalized polymers but no collagen.

The present invention is different from the U.S. patent to Hai-Quan, Mao and al. No. 2005/0,058,692 which uses collagen as a ligand biomolecule for a synthetic polymer matrix.

In the present invention, for the first time we demonstrate that the terminal differentiation of the contractile cell may be obtained in collagen matrices by the simple fixation onto these matrices of adhesion peptides such as RGD peptide. The spontaneous or otherwise stimulated contractile activity is increased as well as the electric threshold, these factors being crucial as the implanted myocardium after implantation should be stimulated by the native cardiac muscle so that the contractions can consistently occur. The applicant further proposes a solution to delay the inflammatory response and the immune response against the graft through chemical non toxic cross-linking procedures. The RGD peptide fixed onto the collagen matrix also favors the in vitro and in vivo angiogenesis. It is known indeed from Levenberg S. and al (2005)[101] that local pre-vascularization or angiogenesis are important factors to promote the implant functionality and the survival of the associated cells.

The agent may be a chemical, a physical, a biological agent or combinations thereof. It may be for example a growth factor, a mechanical force (including but not only external interactions, shear stress and mechanical stress), electric stimuli, voltage, magnetic field, biomolecule and small molecule or combinations thereof.

Particularly interesting are agents which control the cell adhesion, survival, proliferation, apoptosis and differentiation. They may be agents controlling the angiogenesis, ischemia, degradation, turnover and immunogenicity of the extracellular matrix, the inflammatory or immune response, the cellular homing, the tumor cell proliferation, the myocardial, vascular or tracheobronchial and pulmonary function. As regards the biological agents, the agent or the receptor(s) thereof may be equally used.

As used herein, a so called "agent" further includes collagen, fibrin or fibrinogen, a cytokine, a chemokine, eicosanoides, glycoproteins, glycosaminoglycans (for example heparin/heparane sulfate (for example hereabove included syndecane 1; 2; 3; 4), chondroitin (hereabove included not exclusively chondroitin 4 and 6)/sulfate dermatane or sulfate keratane), keratane and chemotactic agents, a growth factor receptor, an enzyme, a hormone or its receptor, an angiogenic factor, a factor for promoting or inhibiting vascularization, a vaccine antigen, an antibody, a coagulation factor, a normalization protein, a transcription factor, a differentiation factor, a receptor, DNA, cDNA, DNA-aptamers, a toxin, a structural protein, an adhesion molecule, a drug, a therapeutic agent, a chemotherapeutic agent, an antibiotic, antifungals and antibacterials, antiviral agents, antimicrobials, anti-infectious agents and any fragment, variant or combinations thereof.

In a specific embodiment, the coating of this agent creates spatial opportunities for depositing a biologically active agent intended to treat ischemia or any heart dysfunction, such as alpha or beta-adrenergic blocking agents or agonists, AMP kinase-activating agents, angiotensin converting enzyme (ACE) inhibitors, angiotensin II receptors, antiarrythmic agents, anticoagulants, anti-platelet aggregation agents, antidiabetic agents, antioxidants, anti-inflammatory agents, billiary acid sequestering agents, calcium channel blockers, calcium antagonists, CETP inhibitors, cholesterol and lipid regulating agents, drugs which inhibit the conversion of arachidonic acid, diuretic agents, estrogen replacement agents ionotropic agents, fatty acid analogues, fatty acid synthesis inhibitors, fibrates, histidines, nicotinic acid derivatives, nitrates, agonists or antagonists to peroxisome proliferator-activated receptors, ranolzine, statin, thalidomide, thiazolidinediones, thrombolytic agents, vasodilatators and vasopressors and other lists of SDF-1 factors, mesenchymal factors homing cells such as alpha MCP-3, OEB, TGF-alpha or -beta superfamily ligands, LIF chemokines, BMP chemokines, BMP receptors, etc., a signaling molecule such as smad or Idb3, BMP2, BMP4, . . . , also included, but not exclusively, drug, a growth factor selected from activin-A (ACTE), retinoic acid (RA), epidermal growth factor, bone morphogenetic protein, tumor growth factor TGF like "TGF-.beta", HGF (hepatic cell growth factor), PGDF (platelet-derived growth factor), albumin, heme oxygenase, LDL (low density protein), alpha. (tumor necrosis factor), insulin-like growth factor (IGF-I and/or II), fibroblast growth factors, nerve growth factors (NGF), muscle morphogenic factor (MMF), alpha-chemokine stromal cell-derived factor (SDF)-1, VEGF (vascular endothelial cell growth factor), fibroblast growth factor (FGF) or receptors, hematopoietic growth factors, heparin, heparane sulfate, chondroitin sulfate, glycosaminoglycan, anticoagulants, thrombolytic agents, antifibrinolytic agents, antiplatelet agents, coagulation factors, tissue plasminogen activator (t-PA), thrombomodulin, high molecular weight kinogen, AT-III, C1-esterase inhibitor, H factor, erythropoietin, SCF (stem cell growth factor), G-CSF (granulocyte growth factor), GM-CSF (granulocyte-macrophage stimulating factor), complement protein, platelet-derived growth factor (PDGF), monocyte chemo-attracted protein-1 (MCP-1), epidermal growth factor (EGF), parathyroid hormone (PTH), serotonin transporter or serotonin receptor transporter or serotonin receptor antagonists and agonists, endoglobulins, endothelial cell growth factor, stimulating factors, angiogenic CXC of endothelial cells chemokines, HIF-1alpha, angiogenin, heparin-binding growth factor, peptide growth factors, insulin, IGF (insulin-like growth factor), estrogen, human growth hormone (hGH), follistatin, proliferin, prostaglandin, interleukins or receptors, globins, immunoglobulins, histocompatibility antigen of the HLA type, catalytic antibodies, tumor necrosis factors, chemokines, immunosuppressants, anti-inflammatory agents, antineoplastics, antibiotics, antifungal and antibacterial agents, antiviral and antimicrobial agents, anti-infectious agents, leptins, interferons, colony-stimulating factors, V-MAP, angiopoietin, latency-associated peptide receptor (such as LAPβ1, LAPβ3) for growth factors or cytokines, VEGF-1, VEGF-2 (KDR), CTGF, Tie-1, Tie-2, SCA, CD133, CD34, CD43, ephedrines, proteins for controlling the matrix degradation such as metalloproteinases (MMP) type proteins, MMP 2, Del 1, alpha HIF-1, monocyte chemotractant protein (MCP-1), oligomer regenerating agents (RGTA), nicotine, glycosaminoglycan such as heparin/heparane sulfate or chondroitin sulfate/dermatane/keratane, laminin or peptides containing the laminin YIGSR ligand unit, IKVAV sequence, elastin VAPG sequence, heparin binding domains based on X-B-B-X-B-X or X-B-B-B-X-X-B-X sequences, B-B-X-B sequences, wherein B is an amino acid and X is a hydroxy-amino acid, proteoglycans or molecules aiming at binding proteoglycans (such as HepII-binding heparin domain of fibronectin for example), REDV, PHSRN, RGD, FHRRIKA, adenosine and inosine alone or in combination, adhesion molecules or receptors for adhesion molecules (not exclusively ligands identified by integrin receptors but also other cell adhesion-mediating receptors or co-receptors).

The associated agent may be chemically bound, adsorbed, absorbed or be free.

The agent may be contained within the volume of or be external to the 3D-scaffold within a tissue or in an external scaffold or in a medico-surgical device as defined for the secondary scaffold and which aim is to treat the first scaffold or the tissue contacting the same.

The agent may be present in the 3D-scaffold in vitro or in vivo before, during or after the 3D-scaffold implantation period.

The agent can be delivered by an external contention system, endovascular or endobronchial device, tissular or endocavitary device.

The scaffold creates within the tissue localized niches for depositing a biologically active material therein. The tissue enables to concentrate the binding of the biologically active material such as drugs which are locally or systemically introduced thereto. The scaffold may also act as a device for releasing the bioactive agent associated with the scaffold.

A population of cells may be associated or not with the modified collagen three-dimensional support. Under some circumstances, the cell population may result from the colonization of the support performed by the cells of the host. The cells may be embryonic, fetal, neonatal or adult cells. The cells may be stem cells, pre-differentiated stem cells, progenitor cells or differentiated cells or a combination thereof. The cells may have an autologous origin, be homologous cells, heterologous cells such as mammalian cells.

The cells may be genetically engineered. The cell component wherein the cells were engineered to provide a bioactive agent. The cell component wherein the cells were engineered ex vivo or in situ or combinations thereof The cell component may be obtained by fusing together different types of mammalian or non-mammalian cells. The cells may have various differentiation degrees, be activated or not, be variously aged, be engineered or not, or may result from combinations thereof.

The cell different types may be associated.

One or more types of cells may be present in the 3D-scaffold. The distinct cell types are not necessarily associated with each other and present at the same time in the scaffold. The cells may be initially associated with the scaffold in vitro or in vivo. The cells may be cultured in the scaffold in vitro before implantation. The cells may be associated secondarily with the scaffold. To colonize the support, the cells may for example be injected directly into the scaffold, near to or spaced apart. The support may thus be for example injected by the endovascular route and the cells may be injected concomitantly or secondarily. The presence of the cells in vivo may also in some situations precede the placing in the scaffold. Sometimes, the associated cell population may result from the colonization of the support by the host cells. The association of the various application combinations thereof is possible.

The method includes but not exclusively cells that are potentially rhythmic, angiogenic or contractile, such as human embryonic stem cells, embryonic stem cells from human SCNT-derived blastocytes (nuclear transfer), purified adult stem cells derived from a differentiated tissue: from liver, pancreas, heart, lung, marrow bone, muscle tissue (smooth, cardiac, skeletal muscles, etc., progenitors for endothelial or contractile cells isolated from fetal, neonatal or adult tissue such as Sca1 cell +/− isolated from pancreas, heart, liver or any other fetal tissue, in vitro or in vivo pre-differentiated cells, skeletal myoblasts or myocytes, cardiomyocytes (fetal, neonatal, adult), cardiomyocyte or myocyte progenitors, human marrow mesenchymal cells, stromal cells, hematopoietic cells, progenitor cells isolated from umbilical cord blood, blood leucocytes and blood progenitor cells for cardiac myocytes or endothelial cells (such as CD34+, AC133+ cells), amniotic cells, placenta cells, trophoblast cells, basal cells, adipose tissue cells or derived cells, cells purified from omentum such as epiploic mesothelial cells, periosteal cells, perichondrial cells, fibroblasts, neuronal cells, hippocampal cells, epidermal cells, dermal cells, keratinocytes, granule cells, immune system cells, pre-differentiated cells (using electric treatments, hypoxia, hypothermia or freezing, by stimulating or removal of some chemokines, chemical products, biological products and other physico-chemical treatments).

In the following examples which relate to a particular embodiment, the various steps of a modified collagen matrix will be described, as well as the characteristics of the thus obtained preparations.

EXAMPLE 1

Covalent Coupling of Adhesion Molecules Such as RGD/RGE Peptides to the Collagen Scaffold or Biological Agents Such as Proteoglycans, Growth Factors or Cytokines if the Scaffold is Made of Collagen and/or Contains Thiol, Amine or Carboxyl Accessible Groups.

The coupling chemical reaction principle is illustrated in FIG. 1. The coupling described here makes it possible to illustrate the RGD moiety at a medium distance from the support, here a 30-40 Angstrom collagen matrix, elongation that is favorable to the maximum interaction of the peptide sequence with the integrin receptor site (cf. Beer J H. and al. 1992, Craig W S. and al. 1995)[23,24].

Collagen scaffolds are used, and advantageously DHT-cross-linked porous supports like with ULTRAFOAM®, materials that are already used in clinical medicine as hemostatics: 5 mm-thick ULTRAFOAM sheets (2.5 mm after rehydration in PBS) (Davol Inc., Cranston, R.I.) come from beef, DHT-cross-linked type I and type III collagen fibers. Matrices, after rehydration are cut in disks of 8 mm diameter and 2.5 mm thickness by using skin biopsy punches. The collagen concentration in the support after rehydration is of about 20 mg/cm$^3$. The support pore size does range from 30 to 200 µm (H. Park 2005)[56]. RGD linear peptides (for example GRGDS) or RGES (Sigma Aldrich) were covalently bound to the collagen matrix after formation of the collagen matrix by using a water-soluble heterobifunctional cross-linking agent, (6-[3'-2-(pyridyldithio)-propionamido]hexanoate (cf. (Sulfo-LC-SPDP) (Pierce Biochemical (Rockford, Ill., USA)).

Such heterobifunctional cross-linking agent (also called crosslinker) does react through its N-hydroxysuccinimide group with the amine groups present on collagen. The other crosslinker end which contains the 2-pyridyl disulphide group does react, after conversion to a thiol group through dithiothreitol, with the activated adhesion peptide. This peptide, advantageously GRGDS, has been coupled extemporaneously with the crosslinker sulfo-LC-SPDP on the N-terminal part of the glycine residue or on the arginine residue if using RGES. For example, GRGDS or RGES (sterile aqueous solutions) (0.1-10 mg/ml) are reacted with Sulfo-LC-SPDP for 24 h to 72 h to give respectively Sulfo-LC-GRGDS and Sulfo-LC-RGES. Separately, Sulfo-LC-SPDP in excess (25 µl, 50 µl and 100 µl of 20 mM of a stock solution for 10 mg of collagen matrix) are reacted at room temperature for 24 h to 72 h under constant stirring with the rehydrated collagen matrix in PBS pH 7. The crosslinker in excess is removed by successively washing the matrix in PBS. The thus modified matrices are treated with dithiothreitol (DTT) (12 mg/ml in PBS) and DTT is removed by washing. In the final reaction, the previously treated collagen matrices (10 mg) react with Sulfo-LC-GRGDS (0; 0.5; 1 and 2 mg) or Sulfo-LC-RGES (1 mg), 48 hours in PBS. The substitution degree is monitored by modifying the relative amounts of the various reactants as compared to collagen and above all by spectrophotometrically measuring pyridine-2-thione resulting from the crosslinker cleavage (specific molar absorption=$8.08 \times 10^3$ M$^{-1}$ cm$^{-1}$ at 343 nm) (FIG. 1). The preparations are maintained sterile and kept at 4° C.

EXAMPLE 2

Using Collagen Scaffolds Functionalized with Adhesion Molecules for Making a Contractile Tissue Contractile Cells Different cell types have a contractile activity prior to or after a complete differentiation as for example smooth muscle cells, skeletal muscle cells or cardiac myocytes. Embryonic stem cells, pre-differentiated or not (where the differentiating agent may be for example a growth factor or a combination of growth factors. The removal or the inhibition of some factors from the culture medium as for example growth factors of the FGF, TGF beta, BMP-2, SDF1 type, physical factors such as hypoxia, electrostimulation, freezing, mechanical stress, etc.) also has shown their ability to promote the differentiation towards contractile cells. Marrow bone cells (hematopoietic cells or mesenchymal cells), cells isolated from the circulating blood (also including cells isolated from the umbilical cord blood). Contractile potential cells were also isolated from differentiated tissues (fetal or adult tissues), from muscle tissues (like myoblasts or cardiomyoblasts), progenitors isolated from adipose or epiploic tissues, from fetal or adult differentiated tissues (as for example liver, pancreas, myocardium, lung, etc.), amniotic fluid, genetically modified cells, etc.

Injecting Cells into the Collagen Support:

In this example of differentiated contractile cells classically used, neonatal rat cardiac myocytes (obtained by digestion of newborn rat heart ventricle within the two days which follow the birth) were set in place in collagen matrices that had been functionalized or not with adhesion peptides. The collagen matrices were obtained by DHT. The following example relates to a ULTRAFOAM™ (Bard) type commercial matrix, but other types of matrix comprising a collagen component may be used. A great number of cells $1\ 10^7$ cells/$cm^3$ of collagen matrix were thus placed in the matrix. For comparison purposes, the number of cardiac myocytes in the myocardium, related to the myocardial tissue volume is of $0.5$-$1.10^8$ cardiac myocytes /$cm^3$ (ref. M. Radisic and al. 2003)[102]. The collagen scaffolds modified through adhesion peptides (size: 8 mm of diameter ×5 mm of thickness) were seeded with $2\times10^6$ cardiac myocytes to a concentration of $1.5\times10^7$ cells/$cm^3$. Immediately after the cell deposition, the matrices were centrifuged at 1000 revolutions/min. for 6 min. so as to improve the efficiency and homogeneity of the cell distribution. Non fixed cells that were present in the pellet were deposited again on the top of the matrix.

Culture of the Cellularized Scaffolds

The cellularized matrices were then transferred to 12-well plates and cultured under static conditions without any bioreactor but using a classical culture medium DMEM 2 ml (Dulbecco's modified Eagle's medium) enriched with 10% of fetal calf serum without using equine serum as is usually required. After 24 h the culture medium was replaced with DMEM only containing 5% of fetal calf serum as well as transferrin (10 mg/ml), insulin (1 mg/ml) and selenium. The culture medium was changed twice a day to day 8. It should be emphasized that there was absolutely no need for any MATRIGEL™ type extracellular matrix, for any physical stimulus like a chronic electrostimulation or a mechanical stress, for any bioreactor or for the use of high concentration of any xenogeneic serum such as equine serum to achieve the obtained results.

Histology

The cellularized matrices were fixed on day 8 in 10% formalin then embedded in paraffin to perform a classical histology. 5 µm-transverse sections were marked with a HES (haematoxylin-eosin-saffron) staining for the structural analysis and to determine the number and the distribution of the cells. A portion of the cellularized matrices was also frozen in liquid nitrogen to conduct immunolabeling. After thawing, the sections were permeabilized with triton X-100, saturated with PBS containing 3% of bovine serum albumin. Primary antibodies, then secondary antibodies conjugated to a fluorescent label (Alexa) were then incubated together with the sections. The RGD modified matrices were thus incubated with a mouse anti-alpha-actinin antibody (use concentration 1:500 dilution (Sigma)) and an anti-mouse secondary antibody conjugated to alex-546 (Molecular Probe) (1:300 dilution). The cell nuclei received a DAPI specific labeling.

The injection of neonatal rat cardiac myocytes into a collagen matrix that was modified with adhesion peptides enables to prepare an implant which contracts spontaneously after a culture in vitro for ≈2-3 days. On day 8, a contractile activity was observed for 50% of the collagen-containing implants in the absence of RGD moiety and for 80% in the presence thereof (p=ns). Interestingly, spontaneous pulsations are more rapid in the presence of the RGD moiety 141±17 versus 61±26 (significant difference p<0.05. When present, these pulsations are also more regular in the modified collagen matrices.

Figure 2:
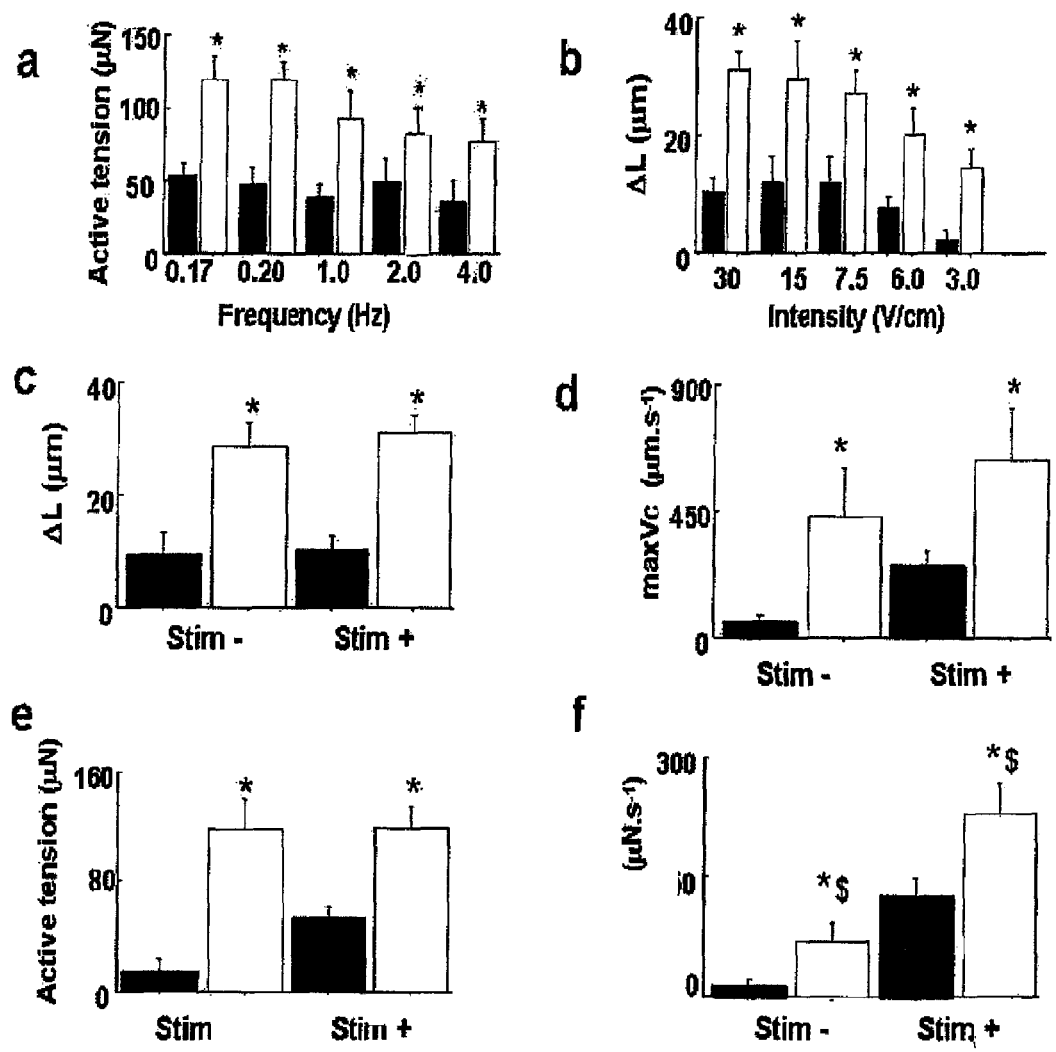
Figure 3:
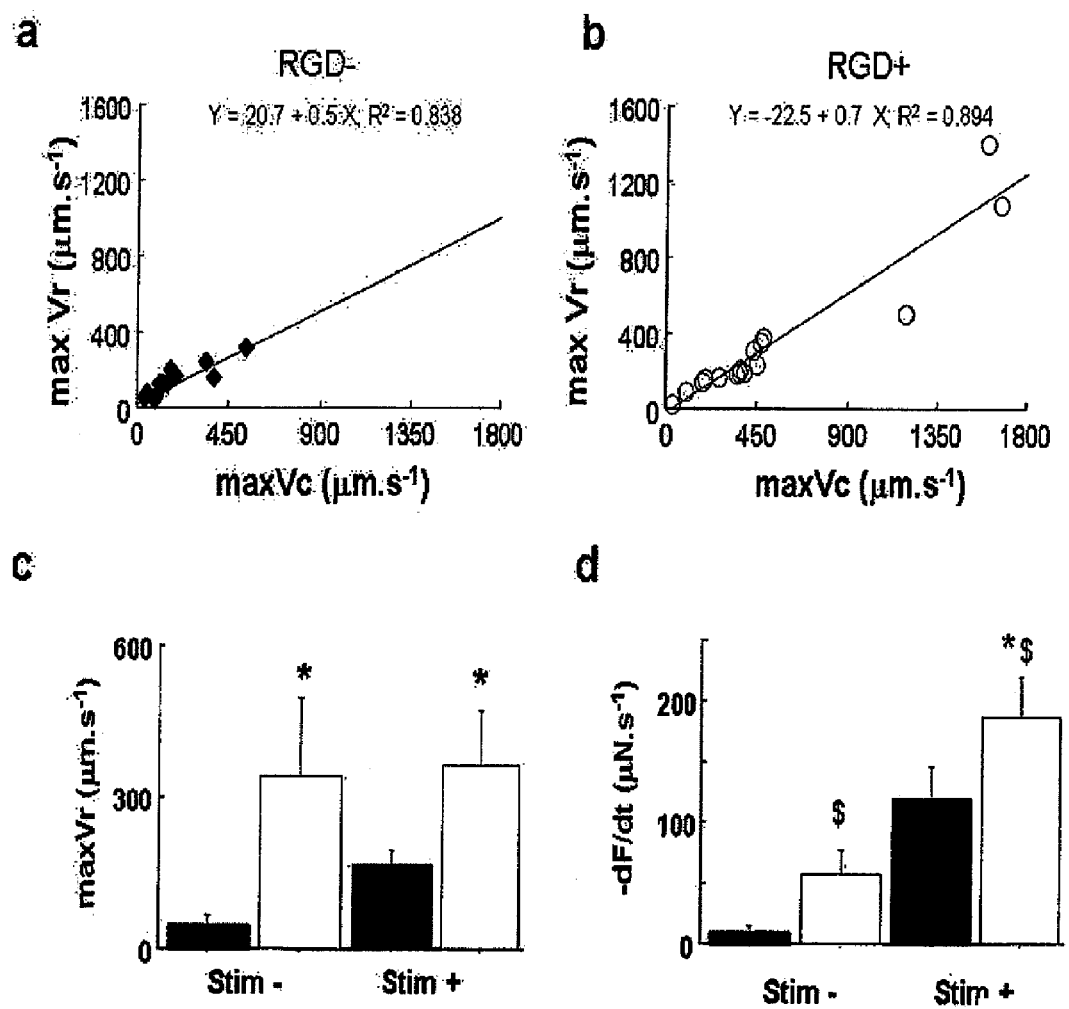

The various contractility parameters are illustrated in FIG. 2 as regards the contraction parameters or in FIG. 3 as regards the relaxation parameters. Spontaneous activities without electrostimulation (Stim−) or with electrostimulation (Stim+) were recorded according to the technique of Y Lecarpentier and al.[103-105]. The filled histograms do correspond to basic collagen matrices and the empty histograms to the collagen matrices functionalized with RGD moieties. Records were performed on day 8.

FIGS. 2a and 2b show the effect of an electrostimulation on the matrices. The measured parameters were either the strength of the developed force in micronewton (cf. "active tension") or the shortening results ($\Delta L$). As can be seen when the electrostimulation frequency increases, the developed forces decrease which does express a negative stercaire effect. However, whatever the stimulation frequencies tested, the developed forces in the presence of the RGD moiety are higher than the developed forces in the absence thereof (FIG. 3a). The maximum developed force is measured with a frequency of 0.17 Hz. Indeed, there is for the matrices an electrostimulation threshold which depends on the frequency. We further observed that for a same electrostimulation intensity, electrostimulation frequency threshold is lower for matrices with RGD. The mechanical responses are also better in the presence of the RGD moiety (where each p means p<0.05) (FIG. 2b). For RGD matrices, stimulation thresholds are very low (lower than 3V/cm). These thresholds are approximately of the same order than the spontaneous depolarization that can be measured at the myocardium level. The ability of the implanted contractile tissue to synchronize with the native myocardium of the patient will be all the more efficient that the stimulation threshold of this tissue will be low, which is the case in the presence of RGD. The various parameters spontaneous contractility, that we measured, are also better in the RGD+ matrices (p<0.01) for both the shortening parameters (($\Delta L$) (FIG. 2c) and for the intensity of the developed forces ("Active tension") (FIG. 2e). Interestingly, with the modified matrix, the measured forces were higher than all the values reported in literature. For an optimum stimulation frequency, the presence of the RGD moiety causes an increase by a factor of 3 for $\Delta L$ (31.1±3.1 vs 9.4±3.9 $\Delta$m (cf. RGD− vs RGD+ respectively, p<0.05). Such difference remains even if the matrices are stimulated (FIGS. 2 c, e Stim+ vs Stim−). FIGS. 2d and 2f illustrate some data as regards the development rates of these forces or these shortening effects as a function of time. It can be seen that both the maximum shortening rates (maxVc: max contraction rate) (FIG. 2d) and the maximum developed force within a given time period (FIG. 2f) are also higher in RGD matrices. The maximum contraction rate maxVc (633.0±180.8 vs 56.8±23.1 Δm/s (cf. RGD− vs RGD+ respectively, $p<0.05$) and the force variation as a function of time was also increased by a factor of 2 in the RGD matrix + as compared to the other type of matrix (FIG. 2f, $p<0.01$).

As for the contraction parameters, the relaxation parameters are improved in RGD+ matrices (FIG. 3) for both the lengthening or the decrease in the muscular tension. In addition, as for the contraction parameters, the implementation of this relaxation max Vr: maximum relaxation rate and −Df/dt rate "decrease in the active tension" (FIG. 3d) is higher in the modified matrices. Such difference also remains under electrostimulation.

FIGS. 3a and 3b compare the max contraction rate Vc and the max relaxation rate Vr in the basic collagen matrices FIG. 3a or in the matrices modified with RGD peptides FIG. 3b. For both types of matrices, there is a strong linear correlation between the contraction and relaxation rates. These rates besides are substantially the same for a given type of matrix. Contraction is an active phenomenon caused by the contraction of the cells. On the contrary, relaxation is a passive phenomenon which may result from the elastic compliance of the matrix support or an active phenomenon due to the cells. The mechanical properties of basic, non cellularized RGD matrices are more or less the same. The relaxation difference obtained between RGD+ and RGD− matrices cannot be due to a resilience difference between the two types of matrices, but rather to the cell population associated with the matrix which is responsible for such difference. Also interesting is the fact that, because the contraction rate and the relaxation rate are very similar, it can be inferred therefrom that the matrix effect is virtually nil, for both the matrix inertia upon contraction and the possible elasticity upon relaxation. Both the contraction parameters and the relaxation parameters are critical for the myocardium filling during diastole.

The histological analysis of the different matrices does confirm a better differentiation of the contractile cells in RGD matrices. After eight days, the collagen tissues with no RGD practically only contain poorly differentiated round cells, with virtually no contact with the matrix at all. On the contrary, cardiac myocytes associated with RGD+ matrices are much more aligned, elongated, with a very regular and central nucleus. Moreover, cardiac myocytes in collagen matrices (RGD+) have an arrangement that is not anarchical at all and are well organized around collagen fibers to which they do strongly adhere. The assessment of the cell number in FACS matrices shows that the cell number decreased in culture. However, such decrease is by a factor of 6 after 8 days in the collagen matrices whereas it is only by a factor of 2 with RGD+ matrices ($p<0.05$ RGD+ versus RGD−). Thus, RGD+ matrices comprise a greater number of cells on day 8 as compared to RGD− matrices ($0.67 \times 10^6$ versus $0.20 \times 10^6$ cells RGD+ vs RGD−, respectively, $p<0.05$). In the same way, in histological sections under a confocal point of view after DAPI-staining of the nucleus for labeling, the cellularized RGD+ matrices have a greater number of nuclei per section in histological sections. Very importantly, cross striations of the cardiac myocytes, which reflect the terminal organization of the cardiac myocyte contractile apparatus, were detected on RGD+ constructs but not on RGD− constructs. Cell morphological changes do not depend neither on the initial number of cells, nor on the cell density in a given preparation, which tends to demonstrate that the differences observed are for the most part due to the cell-support interaction and not to the interaction difference of the cells between each other.

These results indisputably prove that the fixation of adhesion molecules such as RGD peptides onto collagen may facilitate the adhesion, the survival, and the differentiation of contractile cells and thus improve the contractile properties both spontaneously and under electrostimulation of myocardial tissues prepared from these supports. The mechanical performances but also the electrical performances are improved. The tissues are electrically more stable, with lower stimulation thresholds.

EXAMPLE 3

Angiogenesis Induction in vitro by Associating Endothelial Cells in a Functionalized Matrix with Adhesion Molecules:

In another type of preparation, cells of interest such as endothelial cells (mature or progenitor cells) may be transplanted into the functionalized 3D-collagen matrix with adhesion molecules, advantageously the RGD moiety, in the presence of or in the absence of contractile cells or other types of cells as for example fibroblasts, keratinocytes, contractile cells, genetically modified cells, etc. which may also be used independently. This support will promote the survival and the differentiation of the associated cell population as would do endothelial cells. This cell population may be used in association with contractile cells or independently. Such support may sometimes be also used without any initially associated cell population, the cells colonizing subsequently the support. However it has been demonstrated that associating endothelial cells does promote the survival and the differentiation of the contractile cells implanted into 3D-supports (D A Narmoneva and al. 2004[32]) and that the in vitro pre-vascularization of a musculo-skeletal tissue enhances its survival after implantation (cf. S. Levenberg and al. 2005)[101].

The three-dimensional tissues prepared in vitro generally do not have the vascular network which exists in natural tissues. Thus, to become a clinical reality, a contractile tissue prepared in vitro should be able to promote its neovascularization by helping the development of vascularization starting from the pre-existing vascularization of the recipient or by helping the differentiation of an endothelial cell population initially associated with the 3D-support or subsequently recruited in this support after implantation. Thus, one of the most important properties for a tissue prepared in vitro will be its ability to promote its trophicity and the development of vessels inside so as to limit as much as possible the post-implantation mandatory ischemic period which is responsible for an important cell mortality together with a loss of functionality (cf. R Y Kannan and al (2005))[35]. It becomes even more critical with cells that are especially sensitive to hypoxia, as is the case of contractile cells of cardiac myocyte type and when these cells are in addition transplanted into a region wherein the vascularization is from the beginning already altered (ischemic or necrotic myocardium). The implant pre-vascularization and the fact that there is no need for gels in this type of support enable to promote the nutrient free diffusion and thus to produce thicker tissues. Moreover, within this space, the cell microenvironment may be controlled and modified as well as the response of the body. It also enables to associate this support with agents or to transplant into this type of 3D-support cells that have been transformed with genes encoding these agents as is presently the case for the growth factors involved in the regulation of angiogenesis.

Other genes may be of course further associated in a non exhaustive way like those aiming inter alia at promoting the adhesion, the survival, the growth, the "homing", the proliferation, the apoptosis, the differentiation of cells, inside, near to or farther from the three-dimensional support. Also included are genes controlling the degradation or the constitution of the extracellular matrix, or genes that may control the cell depolarization so as to provide them with a rhythmic activity, genes encoding factors that regulate the immune, inflammatory or tumor response.

Association of the Support with "Endothelial Cells":

As opposed to a contractile tissue for which a very great number of contractile cells is necessary, i.e. around 0.5 to 10. $10^7$ cells/cm$^3$, the number of endothelial cells required is much lower with approx. $10^6$ cells/cm$^3$. Mouse mature, differentiated endothelial cells (described by Arbiser el al. 1997) were transplanted into the Mile Sven1 (MS1) collagen matrix (ATCC #CRL-2279). Different MS1 cell concentrations from $10^4$ to $10^7$ were placed into the collagen scaffolds of collagen matrix type functionalized or not with adhesion molecules advantageously the RGD moiety (RGD+ (TR) or RGD− (T)), but also agonist/antagonists peptides such as RGE and cultured in DMEM with 4 mM L-glutamine, 1.5 g/l sodium bicarbonate, 4.5 g/l glucose, 1 mM sodium pyruvate, penicillin, streptomycin and 5% of fetal calf serum (FCS) (Hyclone, Logan, Utah) in 12-well culture plates in an incubator at 37° C. under a 5% $CO_2$ atmosphere for time periods ranging from 3 to 6 weeks. The in vitro angiogenesis development was studied by electron microscopy. Vascular formations can not be seen under the low magnifications obtained with ordinary microscopes, and the presence of vascular structures must be revealed under higher magnification by means of an electron microscopy (EM).

For the electron microscopy, the preparations were fixed in paraformaldehyde, 1.5% glutaraldehyde and 1 mM calcium in 0.1M sodium cacodylate buffer (pH 7.2) at 4° C., thereafter fixed in a buffer with 1% $OsO_4$ at 4° C. and fixed en bloc with 1% uranyl acetate in 50% ethanol prior to being incorporated into Epon-Araldite resins (Electron Microscopy Sciences, Fort Washington Pa.). Thinner sections (60 nm) were made and stained with uranyl acetate and citrate. All the samples were examined using an electron microscope CM-100. Controlling the vascular formation was performed by microscopy with a magnification of (4 k) and the vascular structures were confirmed thanks to an assay with a higher magnification to identify tight junctions and the presence of a basal membrane by varying the Rx ray incidence if necessary. A vascular lumen was defined as a closed space delimited by endothelial cells interacting through cytoplasmic junctions of the "tight junction" type. The number of vascular structure per mm$^2$ was quantified, the complexity of the vessels was assessed by measuring the nucleocytoplasmic ratio of the involved cells, by the average number of cells taking part to the lumen formation and by the branching percentage defined by the number of contiguous lumina and the average number of vascular structures whenever branching. The statistical analysis used the tests for matched series of the Wilcoxon Matched-Pairs Signed-Ranks Test type.

Figure 4:
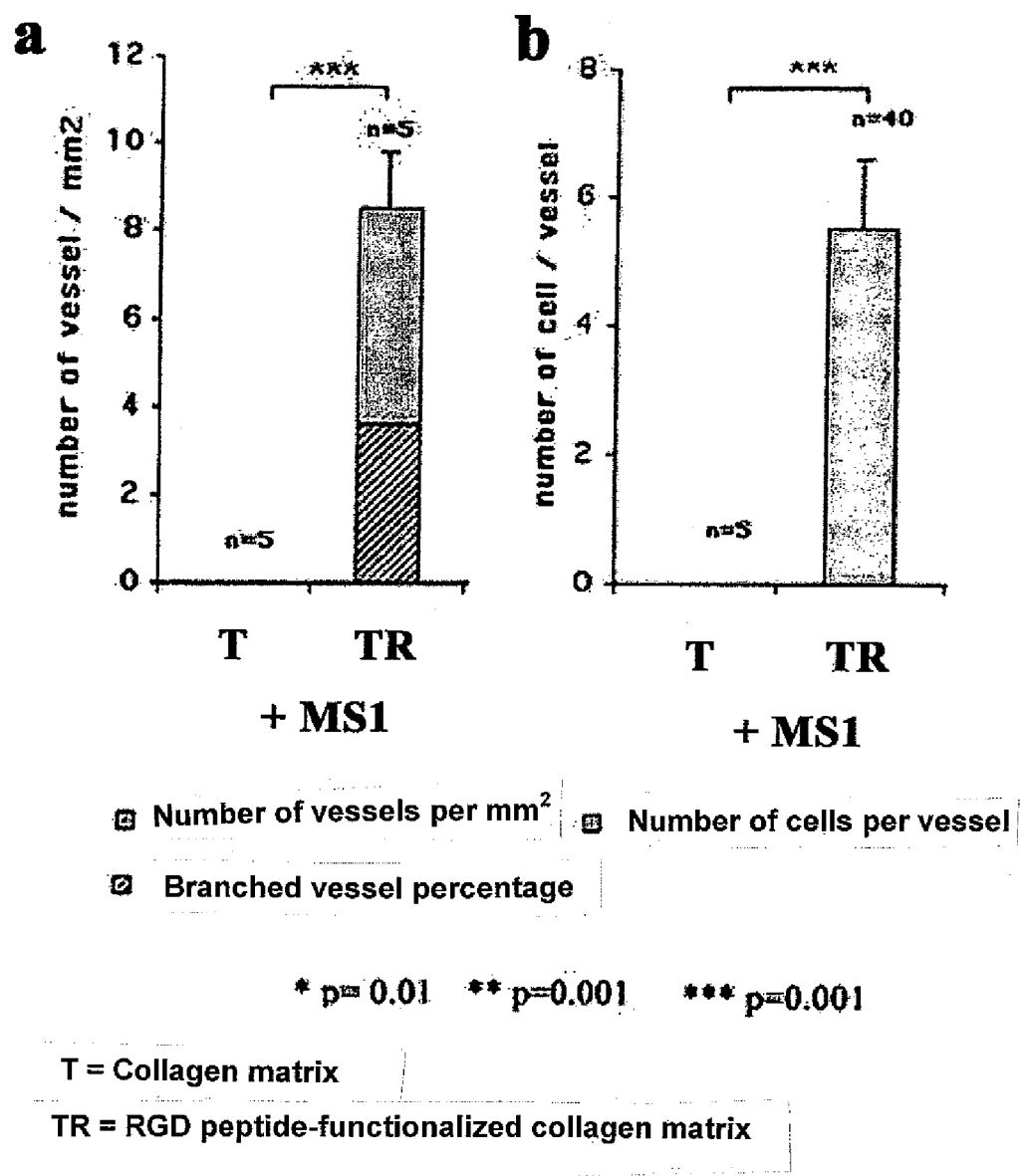

In the collagen matrix functionalized with RGD peptides, the cells did change their morphological appearance by becoming much more spread at 3 and 6 weeks. A cell interaction with the matrix by means of adhesion molecules is responsible for such morphological change of the cell since this appearance change is not due to the initial cell number and is neither present in the basic collagen matrices nor in the matrices functionalized with RGE. Moreover, such modification disappears if the RGD moiety soluble form is associated with the culture medium. In the RGD matrix, endothelial cells are polarized. In addition, there is a basal membrane between the cells and the matrix in some areas. Such basal membrane is not present if cells are cultured in the non functionalized collagen matrices. While obtaining vascular type structures in vitro in usual microscopy ("capillary-like network") in the collagen matrices classically requires the presence of a differentiation agent such as PMA (cf. Ilan, 1998)[36] or the presence of fibroblasts (cf. Black, 1998)[106] or of a medium enriched with factors secreted by fibroblasts ((cf. Montesano, 1993; Baatout, 1997)[107,108], authentic vascular structures do spontaneously develop in RGD matrices, as observed in electron microscopy with in average 8.5 "vascular structures" per mm$^2$ from +/−1.3 to 6 weeks (n=5 separated experiments) (FIG. 4a). In the same time, none of these structures is present in the other matrix types (FIG. 4a). Most of the "vascular lumina" are formed by the cytoplasmic extensions and not by the cell body which contains the nucleus. A careful study of more than 40 vascular structures in RGD+ matrices shows that the average number of cells involved in the formation of a vascular lumen is 5.5+−1.1 (cf. FIG. 4b). Sometimes, vascular lumina are formed by more than 10 interconnected endothelial cells. 23.6% of the vessels are considered as branched (FIG. 4a, hatched portion) with a number of vascular lumina of 3+/0.5 in the case of branching.

EXAMPLE 4

Figure 5:
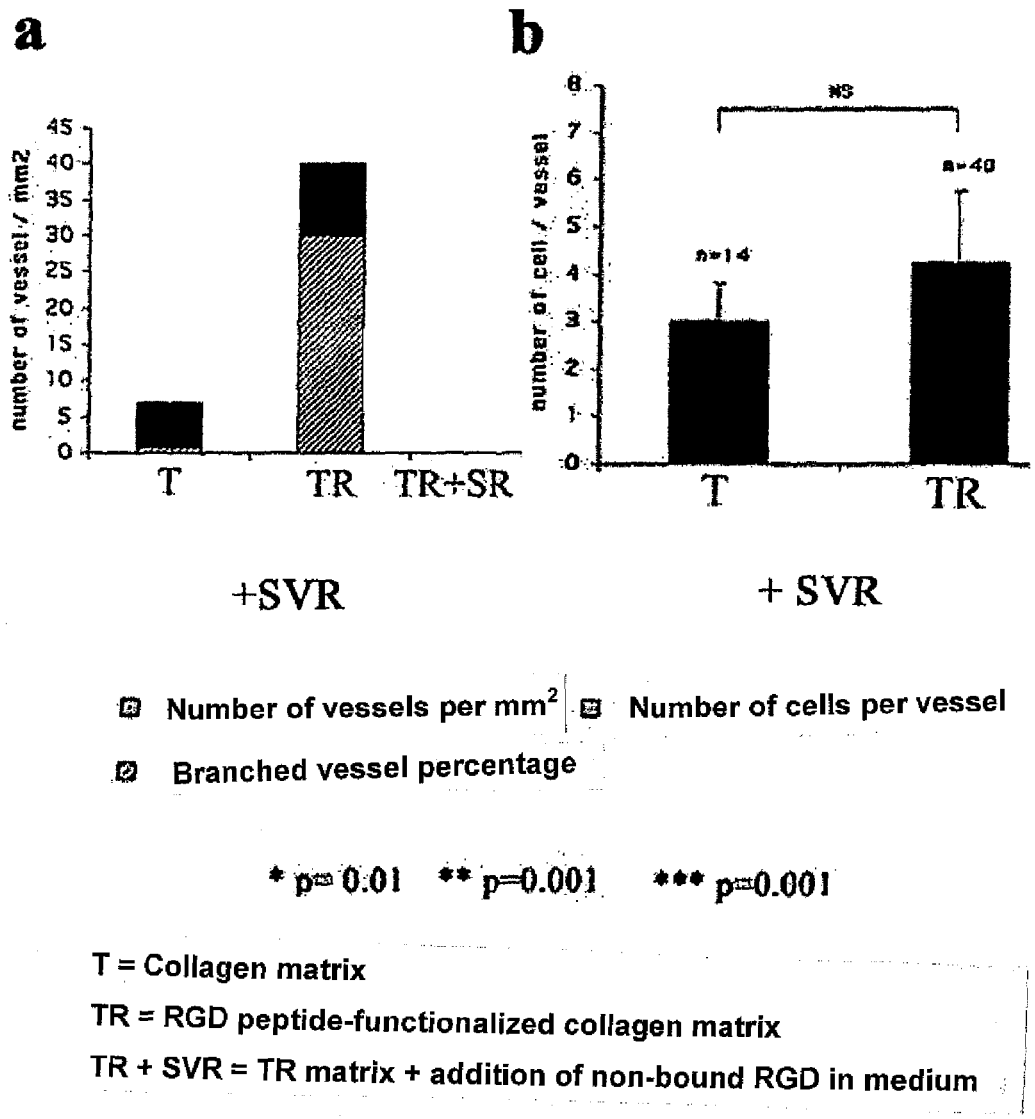

Possibility to Implant Genetically Modified Cells which are Able to Secrete an Agent in the Functionalized Collagen Scaffold:

In the following example, the cells transplanted into the matrix may be genetically modified to release a biological agent involved for example in the angiogenesis, the migration, the survival, the proliferation, the apoptosis, the differentiation, the degradation and formation control of extracellular matrix, the immune, inflammatory or tumor response control, etc. It has been demonstrated that it is possible to genetically modify contractile cells such as myoblasts with genes involved in the angiogenesis like VEGF, angiopoietin, etc. so as to obtain tissues of better quality after transplantation (D. E. Coppi and al. (2005))[109]. In the present case, endothelial type cells (cf. MS1) were modified through viral transfection with the activation gene Ras+. The Ras/Map Kinase pathway was reported as being a crucial activation pathway for controlling the angiogenesis (cf. Ilan and al. 1998)[36]. MS1 Ras+ cells are known as SEVN 1 ras (SVR) (ATCC #CRL-2280) (cf. Arbiser, 1997)[110]. SVR cells (FIG. 5) were implanted and cultured in the different matrices as previously described for 6 weeks. The example shows that the biological activity of the cells may be modified through genetic engineering and that it remains however possible by functionalizing the matrices with adhesion molecules, to influence their behavior and their differentiation degree. Modifying endothelial cells with Ras increases their angiogenic potential since vascular structures and the presence of basal membranes may be observed, even in the basic collagen matrices (T) with around 7 vascular structures per mm$^2$ (FIG. 5a). However even with this type of cells, the angiogenesis remains much more developed if these cells are placed in matrices that have been functionalized with adhesion molecules (TR) (FIG. 5b). The presence of adhesion molecules enables to obtain a more developed angiogenesis as regards both the quantity (number of vascular structures per mm$^2$ ((40 vs 7) (RGD+ vs RGD−) (p significant)) (FIG. 5a) and the quality (% of vessels branched ((75% vs 10%) (RGD+ vs RGD−) (p significant)) (FIG. 5a), as regards to the complexity of the vessels, especially the lower nucleocytoplasmic ratio and a higher number of cells involved in each vascular lumen ((4.5 vs 3) (RGD+ vs RGD−) ((ns)) (cf. FIG. 5b).

EXAMPLE 5

Evaluating the Advantages of Covalently Binding the Adhesion Molecule to the Collagen Support:

To study the importance of the support fixation in the observed effect, the RGD moiety soluble form or the simple RGD moiety adsorption were tested in presence of contractile cells or endothelial cells in collagen scaffolds. RGD high concentrations ranging from 1 to 1000 µg/ml were associated with the culture medium or adsorbed on the matrix for more than 24 h prior to implanting the different cell types. In all cases, the advantageous effects of the RGD moiety on the differentiation and the survival of endothelial cells or cardiac myocytes is obvious. Moreover, even if cells are cultured in a collagen scaffold that has been modified with the adhesion peptide, the presence of the RGD moiety soluble form in the medium does inhibit this effect (FIG. 5a).

EXAMPLE 6

Using the Functionalized Matrix with Adhesion Molecules in the Presence of a Biological Agent.

Some of these agents as for example growth factors may be simply associated with the culture medium in vitro, adsorbed on the collagen support (cf. E J Suuronen and al. (2003))[54] or covalently bound by using or not the means we proposed. The matrix may also be functionalized with proteoglycans for example which are able to retain growth factors. Some of these agents may be for example growth factors, growth factor stabilizing agents (as for example "oligomeric regenerating agents" (RGTAs)), chemokines, contractility enhancing agents, angiogenesis enhancing agents, inflammatory response controlling agents, agents controlling with no degradation or promoting its polymerization, etc. The agent may be present in the support or be administrated to the periphery thereof or to an associated device intended to control the ventricular remodeling for example, or to treat a pathological myocardium. The support may also be used to deliver or concentrate or maintain these agents in a given area. The agent may also be produced by the cells which are associated to the support naturally or after modification. Growth factors are classically used in concentrations ranging from 1 fg/ml to 1 mg/ml (cf. 1-10 nM) (cf. E J Suuronen and al. (2003))[54] although different concentrations may also be used.

In this example, the associated agent is a growth factor aiming at promoting the angiogenesis such as an usual VEGF. The growth factor was associated with the culture medium, but it could also be simply adsorbed on collagen for a couple of hours prior to inserting the cells or be fixed through its NH2 site for example.

Figure 6:
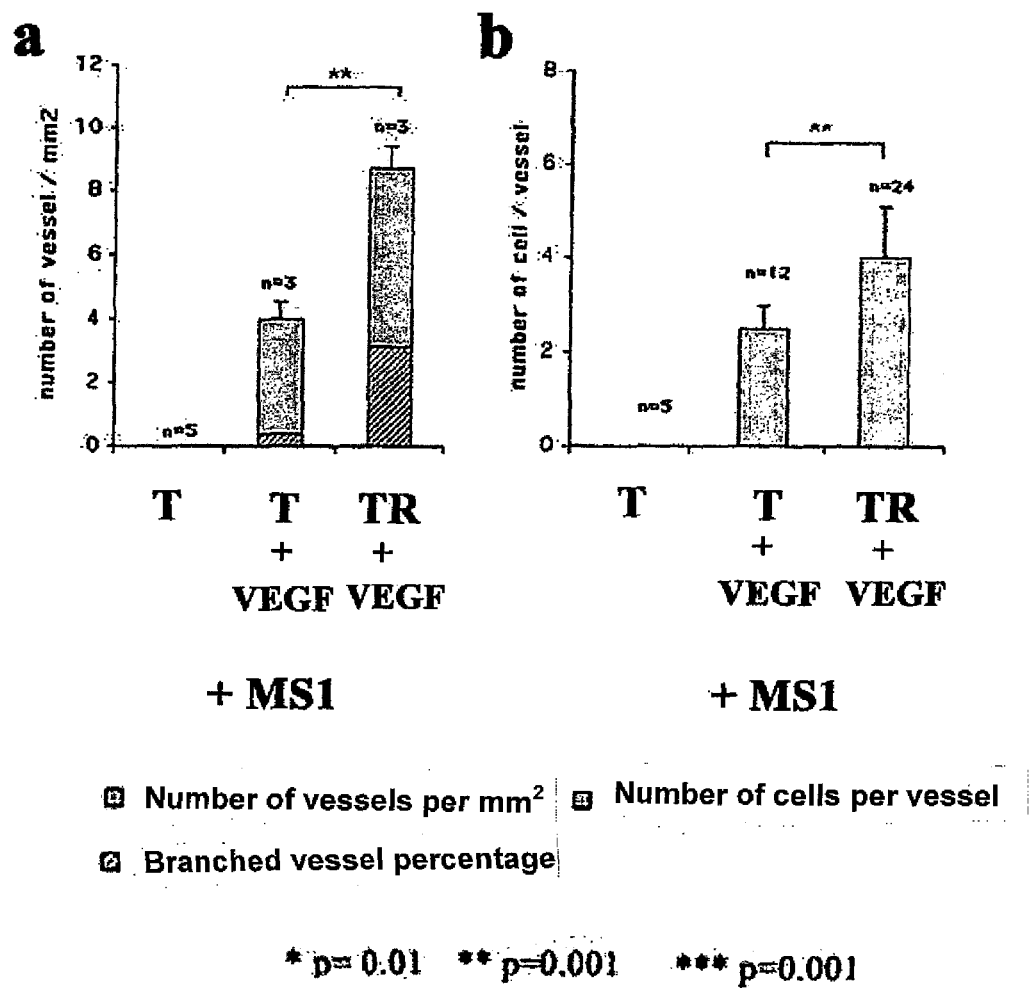

The presence of VEGF (VEGF$_{164}$ (R∝D, Minneapolis, Minn.) in a concentration of 4 ng/ml induces the MS1 cell differentiation with the formation of vascular structures in basic collagen matrices (T), even with no functionalization by adhesion molecules (FIG. 6a). However the absolute number of these structures remains low (average of 3 per mm$^2$), as well as the complexity level thereof: only 2.5+/−0.5 cells (n=12) per vascular lumen (FIG. 6b), with thick-wall vessels (virtually no cytoplasmic extension), only 10% of the structures are branched (FIG. 6a) with, whenever branching, only 2 contiguous vascular lumina. It is known that vessels obtained with VEGF are not perfectly formed and tend to develop vascular extravasations. On the contrary, when the RGD moiety (TR) is present the vascular structure density increases 8.7+−0.7/mm$^2$ (FIG. 6a), as well as the complexity thereof: the number of cells per vascular lumen 4+/−1.1, 25% branching, 3.5 contiguous lumina, whenever branching) (FIG. 6 a-b).

EXAMPLE 7

Collagen Scaffolds Functionalized with Adhesion Molecules Such as RGD Peptides have Anti-apoptotic Effect on Cells that are Associated Therewith.

Integrin receptors, in addition to their contribution to the adhesion of cells to their environment have a key role in that they limit the apoptosis-mediated cell death and increase the number of survival genes (Meredith and al. 1997)[18]. In fact most of adherent cells such as cardiac myocytes, when they loss contact with the surrounding matrix become apoptotic (D. Kuppuswamy and al. (2002))[17]. Part of the cell death could be due to the inhibition of this interaction. This probably partly explains why injecting cells alone into tissues is poorly efficient and induces a high mortality of about 95% which justifies the use of a 3D-matrix at the injection time in order to re-create this environment. However the 3D-support should also possess suitable mechanical properties and specific ligands required for such interaction within the 3D-system.

Apoptosis has been studied in situ by using a Zeiss type confocal microscope and a data integration software (MRC 1024, Biorad). The cell membranes in the matrix were labeled in situ with a red stain. Apoptotic cells were labeled by using an anti-annexin V green fluorescent label (FITC). An apoptosis quantification was carried out by comparing the red fluorescence surface corresponding to the whole cells to the green fluorescence corresponding to the apoptotic cells.

After 3 weeks, the MS1 apoptotic cell percentage in matrices functionalized with the RGD moiety is of 10% versus more than 80% with no RGD moiety. As here previously reported for the cell differentiation, the presence in the medium of the RGD moiety in its soluble form cancels this effect and in both types of matrices either functionalized or not with the RGD moiety, apoptosis returns to 80%. Hence the requirement of fixing the moiety. The low survival of endothelial cells in various types of collagen 3D-support (cf. Ilan and al., 1998, Satake and al., 1998, Goto and al., 1993)[36,37,39] or MATRIGEL type support (cf. Ranta and al. 1998)[38] was already reported by many different groups. The presence of a bound RGD moiety in this type of support would be a means to reduce such cell death and to improve the efficiency of these cell transplantations after injection.

EXAMPLE 8

Controlling the Collagen Scaffold Biodegradation by Means of a Cell Therapy-compatible and Non-cytotoxic Treatment through Fixation with Glutaraldehyde Combined with the Use of a Proteoglycan Such as Heparin or with the Use of Genipin:

The most efficient method for fixing collagen is still a chemical cross-linking through glutaraldehyde. However glutaraldehyde may polymerize and slowly depolymerize, then releasing free glutaraldehyde which is toxic to the cell.

Tissue Fixation with Glutaraldehyde Followed with a Chitosan- and Modified Heparin-based Treatment (Collagen-glut/GAG Matrices)

In the present invention, the inflammatory response against collagen may be reduced in two ways. In the first approach, the tissue is fixed with glutaraldehyde and free aldehyde groups are irreversibly neutralized by using a glycosaminonoglycan (GAG) such as heparin/heparane sulfate, chondroitin sulfate, dermatane sulfate. GAG are known for regulating the hydration degree in matrices but also act as ligands for many growth factors.

The fixation with glutaraldehyde is performed by incubating ULTRAFOAM® collagen scaffolds in a NaCl (50 mM) buffer comprising 0.625% of glutaraldehyde for a month at 37° C. After washing, the collagen scaffolds are placed in a 0.2% chitosan solution (Sigma Aldrich), thereafter 1% glycine (Sigma Aldrich) and 0.02% gentamicin sulfate (Sigma Aldrich) for two weeks at 20° C. A partially degraded heparin solution was prepared by reacting sodium nitrite in the presence of hydrochloric acid (1M, pH 2.0) at 4° C. for 3 hours with heparin sulfate. The solution was then brought to pH 7.4 by N soda and the collagen supports brought into contact with the solution for 12 hours. The collagen preparations were then washed with a NaCl buffer (50 mM), thereafter contacted for 6 hours at 20° C. with a 1% sodium cyanoborohydride solution (Sigma Aldrich) in a NaCl buffer (50 mM) prepared the day before. Thereafter the collagen preparations are washed again and maintained in a solution comprising 1% glycine and 0.02% gentamicin sulfate until their final use.

Fixation with Genipin (Collagen/Genipin Matrices):

Using genipin for fixing fresh or decellularized tissue has already been proposed (U.S. patent Acellular biological material chemically treated with genipin Sung Hsing-Wen and al. 2003). We did follow the procedure proposed by the authors.

0.625% genipin (Challenge Bioproducts CO., Taiwan) in PBS was used, pH 7.4, at 37° C. for 3 days.

In vivo Assessment of Collagen Matrices Treated According to the Previous Methods:

Different types of matrices were implanted into spinal muscles of anaesthetized rats. Histological analyses after 10 days showed a massive infiltration of the basic collagen matrices with inflammatory cells together with a drastic and premature degradation of the collagen lattice and replacement of this matrix with poorly vascularized fibrosis.

In collagen-glut/GAG matrices as in the collagen/genipin matrices, the infiltration is limited to the matrix periphery. Interestingly, these matrices promote the development of a strong angiogenesis in the vicinity of the matrix although the penetration of the vessels to the inside the matrix remains limited. The presence in the matrix of proteoglycans which are known for promoting the adsorption and the presentation of growth factors could partly explain this local strong induction of angiogenesis. After 1 month, all the 16/16 collagen matrices has disappeared even those which initial diameter was the biggest (8 mm). On the contrary, all the collagen-glut/GAG matrices, n=16 or collagen/genipin matrices, n=16 have an unchanged size (p significant) and the cell infiltration remains limited to the periphery. In addition, inflammatory cells are not very numerous in this infiltration.

EXAMPLE 9

Functionalization of a Collagen-glutaraldehyde/GAG Support or a Collagen/Genipin Support by Fixing the Adhesion Molecule:

Such association enables to control the inflammatory or immune response towards a tissue and to select its colonization with cells of interest.

The possibility of modifying matrices with adhesion peptides also has been validated, wherein these adhesion molecules may be associated prior to or after the adjunction of the collagen cross-linking agents. Adhesion peptides such as RGD were fixed onto ULTRAFOAM® collagen matrices by using the procedure described in Example 1, thereafter the matrices were fixed according to the methods described in Example 8. After rinsing in PBS, these matrices were implanted into spinal muscles of anaesthetized rats. Up to 8 matrices could thus be implanted into the same animal.

After 10 days and 1 month of implantation, all the glut/GAG matrices were still present with few resorption, whereas without glutaraldehyde treatment, all the collagen matrices that had been functionalized or not with the RGD moiety had already disappeared. Histological analyses after 10 days could evidence a massive infiltration of the basic collagen matrices with inflammatory cells together with a drastic and premature degradation of the collagen lattice and replacement of this matrix with poorly vascularized fibrosis. The glut/GAG treatment limits the initial cell infiltration of the matrix with inflammatory cells and the degradation of the matrix is delayed, angiogenesis being limited to the periphery. Very interestingly, in presence of adhesion moieties such as RGD moieties (glut/PGA collagen matrices), vessels as well as cells of the surrounding tissue penetrate into the inside of the matrix, even very rapidly, since, after only 10 days implantation, the external ⅔ of the matrix were already colonized and vascularized. An angiogenesis kinetic analysis performed in the matrices thanks to the angiogenesis quantification technique using intravascular injection of a fluorescent label ISL-B4 (Molecular Probes) confirms that matrices get vascularized and that such angiogenesis was initiated even from the second week and had achieved a plateau of about 6% after 3 weeks. Other experiments for longer time periods confirmed that such angiogenesis develops only slowly but, as opposed to what happened with other types of support such as MATRIGEL™ matrices, such angiogenesis does not tend to decrease after a few months. It should be noted that the angiogenesis level of the matrices has to be compared to that observed in surrounding muscles such as spinal muscles, where such angiogenesis accounts for about 3%+/−1%.

There is a cell colonization within the matrix that does not especially result from inflammatory cells. This approach is very interesting because it proposes a first treatment aiming at preventing any 3D-support cell colonization and then, the selection, thanks to selected adhesion molecules, of cells of interest such as, for example, endothelial cells. The presence of a strong neo-angiogenesis within the collagen-glut./GAG matrices that were modified with adhesion peptides demonstrates a very good biocompatibility of this type of implant and suggests a low toxicity that is compatible with its use in cell therapy.

EXAMPLE 10

Use of Cross-linked Collagen Scaffolds Functionalized or Not with Adhesion Molecules Such as RGD Peptides in Cell Therapy:

The ability of transplanted cells to survive and to differentiate in this type of supports was analyzed. More or less differentiated, human or not human cells (stem cells, progenitor cells, mature cells, genetically modified or not genetically modified cells) were thus implanted into the different types of support functionalized or not with RGD peptides. The contribution of these cells to the support angiogenesis was assessed in support implantation model for muscle tissues (skeletal muscle type) and an angiogenesis quantitative analysis method for these supports was developed.

Cells:
mice, mature endothelial cells MS1.
genetically modified, mice mature endothelial cells SVR.

mice stem cells isolated from differentiated tissues. We recently reported the isolation and characterization of isolated endothelial cell progenitors in various tissues during the development of the mouse (cf S. Cherqui, S M. Kurian, O. Schussler and al. (2006))[111]. These progenitors were isolated from a cell fraction having a low adhesion capacity from neonatal mice liver extracts enzymatically digested with collagenase. Cells were collected on day 8 of the in vitro culture.

human mature endothelial cells isolated from the umbilical cord vein wall known as "HUVEC".

endothelial cell progenitors of human origin isolated from the umbilical cord blood.

These cells were prepared as previously described (cf. Crisa and al. (1999) and Hildbrand and al. (2004)[112,113].

In vivo Angiogenesis Model:

The different types of endothelial cells were placed in matrices treated with glutaraldehyde/GAG and modified or not with adhesion peptides such as RGD peptides. Immunodeficient mice were anaesthetized with pentobarbital and the matrices were implanted into their spinal muscles for time periods up to 6 weeks. Eight matrices could thus be implanted in each mouse. Different combinations thereof had therefore been tested in the same animal. Matrices were explanted after various time periods and the angiogenesis in the matrices was quantified.

In vivo Angiogenesis Quantification:

We developed a reliable and reproducible method for quantifying the angiogenesis in vivo. The vessels were labeled in vivo with an anti-mouse endothelial cell fluorescent label MECA32 (University of Iowa, United States) or ISL-B4 (Vector Laboratories, Burlingame, Calif.). After having cut thick sections (200 μm) by means of an oscillating blade "Automatic Oscillating Tissue Slicer" (OTS-4000) (Electron Microscopy Sciences) we used transillumination through the whole matrix thickness to assess the angiogenesis in a given tissue volume. Fluorescence was then studied by using an ordinary fluorescent microscope and the fluorescence intensity was digitized. Depending on the fluorescence intensity, vessels could thus be identified. The intra- and inter-observer variability was less than 10% for a given specimen. Statistical comparisons were effected by using ANOVA type tests or Student tests.

Figure 7:
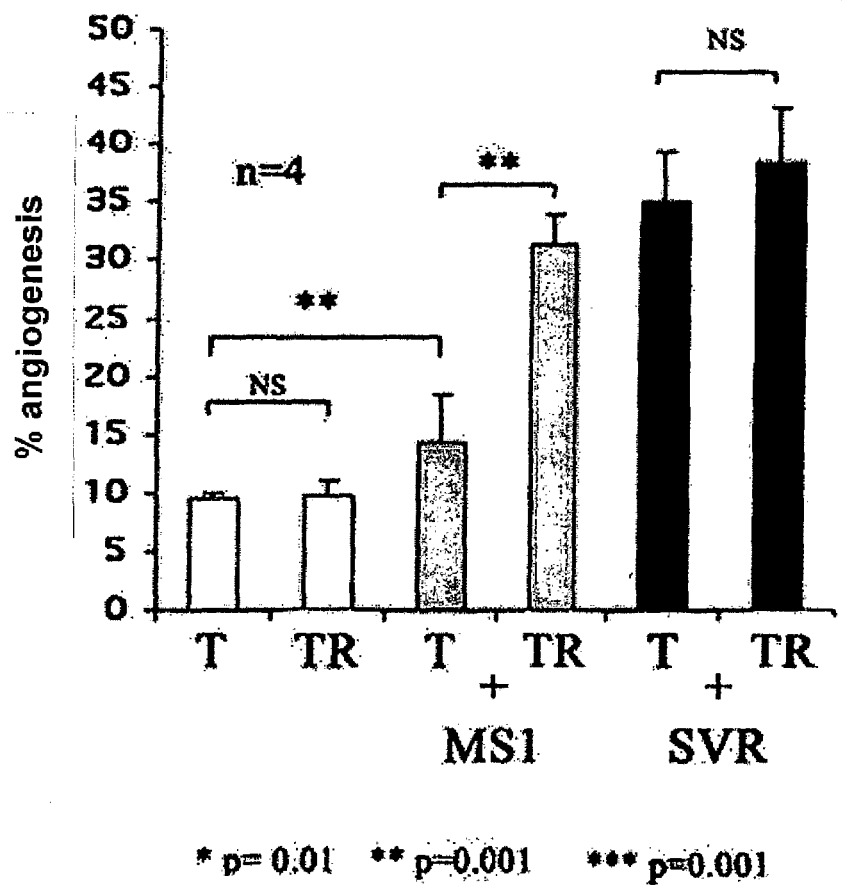

With no association of cell population, the angiogenesis in the collagen matrix remains poor with approx. 8% (FIG. 7 (T or TR)). The presence of MS1 endothelial cells improves the angiogenesis in the collagen matrix with about 14% (FIG. 7) (T+MS1)). Such increase is even more significant if the matrix is functionalized with RGD peptides with 35% (p significant) (cf. FIG. 7 (TR+MS1)). In the presence of the MS1 transformed form (cf. SVR), the angiogenesis is already very important in both types of matrices with approx. 40%. Marrow-derived hematopoietic or mesenchymal cells, leucocytes isolated from umbilical vein blood or from peripheral blood, stem cells, amniotic cells, epiploic cells, adipose tissue-derived cells, etc. all these cells may under particular circumstances contribute to the angiogenesis and therefore be interesting to associate with other cell populations. In the experiments of Crisa L. and al., HUVEC type human endothelial cells could only form very few vessels in collagen matrices (cf. Crisa and al. (1999)[113]. As a validation of this observation, our experiment showed that the angiogenesis level in the matrices modified with the RGD peptide (T or TR) with or without human endothelial cells (HUVEC) was essentially similar (6.7%+/−2.5 vs 7.9%+/−3 ns) (FIG. 8). Very interestingly, the angiogenesis in the collagen matrices may be improved in presence of progenitors for endothelial cells isolated from the circulating blood (cf. progenitors CD34+) up to (22.3%+/−5.5) but only when the matrices were modified with the RGD peptide (FIG. 8). Therefore, this demonstrates clearly the advantage of using adhesion moieties in the collagen matrices with human cells.

Figure 9:
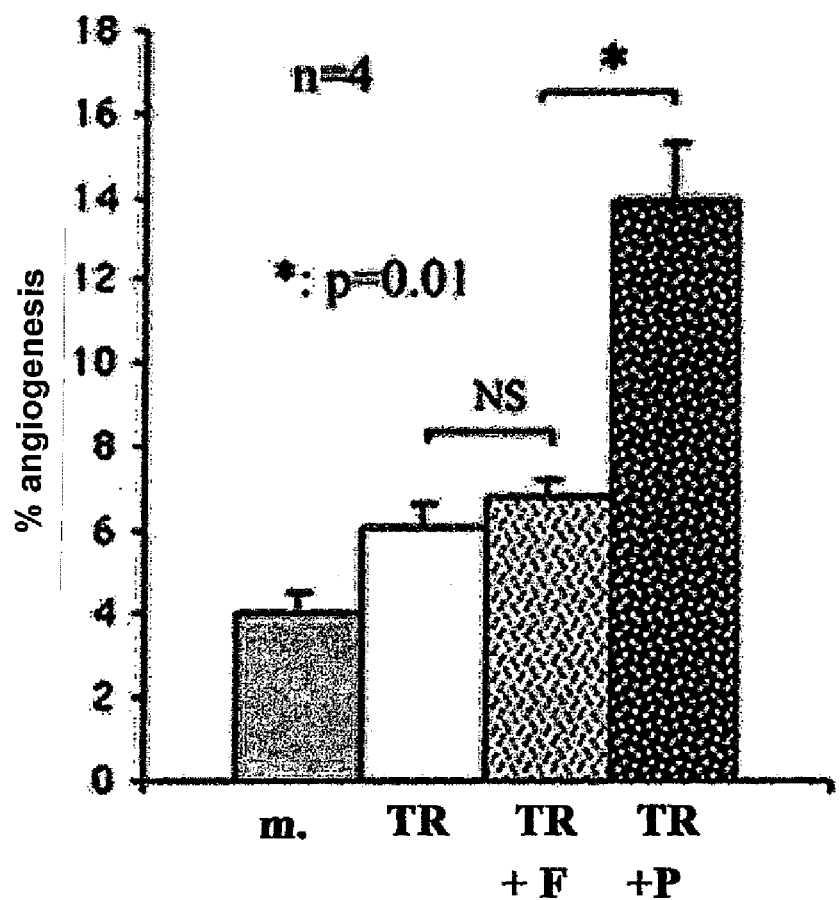
Figure 10:
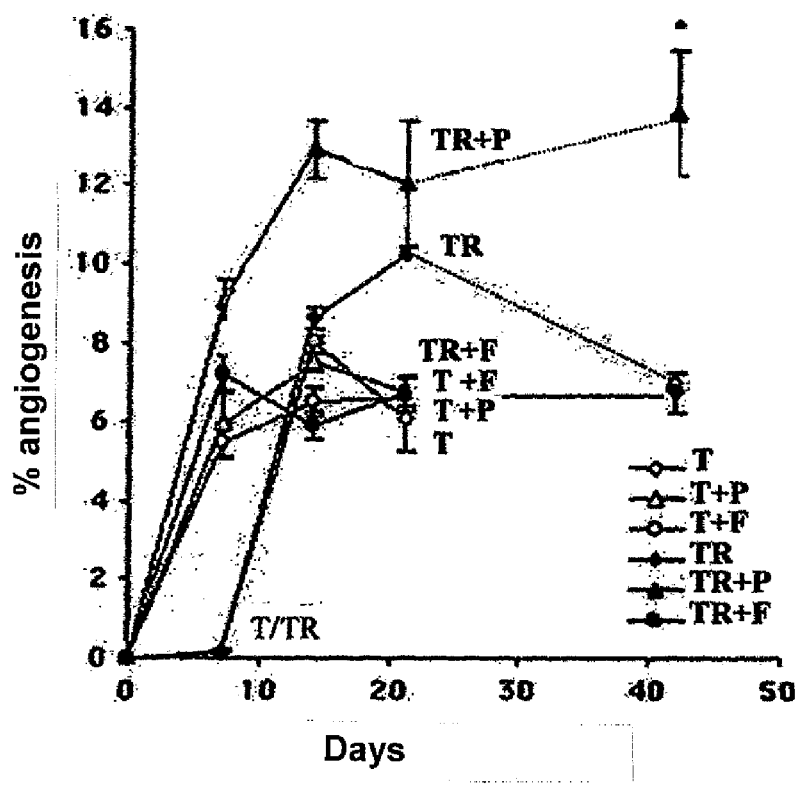

Different approaches are being developed to increase the angiogenesis in three-dimensional environments. Preparations based on fetal tissues may also already contain these cells and the presence of the RGD moiety could promote the survival and the differentiation of these cells. We have recently reported the presence of stem cells, in differentiated fetal tissues, the said stem cells being able to incorporate themselves into the host vascular architecture to promote therein the local angiogenesis (cf. S. Cherqui and al. (2006)[111]. These cells highly depend for their survival on factors secreted by "feeder" cells, essentially fibroblasts (F). On the third week, the angiogenic potential of these feeder cells "F" remains low as compared to that of the endothelial cell "P" progenitors and the angiogenesis obtained is of the same order as that obtained in the matrix with no cell or in the surrounding spinal muscles (FIG. 9). However, as shown in FIG. 10, the presence of a cell population accelerates the initial angiogenesis which is then of 6% on day 7, whereas it is not yet perceptible when there is no cell association. Later, the angiogenesis extent is increased in the matrices modified with RGD peptide, but only in the presence of the endothelial cell progenitor to achieve a steady state of approx. 14%, whereas in the absence of RGD or in the presence of feeder cells, the angiogenesis remains low and stable (FIG. 10).

Applications

The present approach could thus have a double advantage, the first one would be to promote and accelerate the initial angiogenesis using cells having proangiogenic properties and the second one would be to associate to the tissue itself a population of endothelial cells that can differentiate and form vessels in a suitably modified 3D-environment. All of them are parameters which will limit initial post-implantation ischemic phenomena and improve the angiogenesis in ischemic or necrosed areas.

The matrices were implanted into the spinal muscles because these are muscle tissues similarly to the myocardial tissue, and moreover, sometimes, prior to being implanted in contact with the myocardium, the cellularized tissue may also be implanted into well-vascularized ectopic sites, the recipient patient acting in fact as a bioreactor for developing its own tissue. These sites could be for example the cavity of peritoneum especially the omentum, a muscle tissue such as broadest of back for example, the pleural cavity, a subcutaneous tissue, etc. In these sites, different scaffolds could be stacked on each other so as to obtain a thicker well-vascularized tissue[114]. In these different sites various stimuli could be applied (chemical, biological, physical stimuli, etc). These stimuli could be amongst other things electrostimulations which demonstrated their advantageous ability to improve the quality of a contractile tissue, or a mechanical stress. The various stimuli could be or not synchronized with the heart rate of the patient. To apply the "shear stress" the scaffold could be fixed to a support having a varying volume like an inflatable system such as a balloon or a buoy which could have the shape of ventricular cavities, for example. The support could be made of silicone for example so as to limit the adhesion of the matrix to this support. Part of the scaffold could be covered with tissues or devices aiming at limiting the local adhesions to facilitate the iterative operations. After several weeks, the vascularized scaffold could then be transferred to the pericardium to be applied on heart to replace part of or the whole myocardial wall, to treat the myocardial dysfunctions, as a free graft or a pedicled graft[30]. Sometimes, an epiploic flap or a skeletal muscle flap for example could be used either to cover the contractile patch or to transfer said patch into the pericardium. Using a contractile patch may be also associated with the use of other myocardial regeneration methods, such as cell therapy. In the present invention, we suggest to use "modified fibrins" in the various medical and surgical applications wherein fibrin is classically employed. One of the applications thereof is tissue engineering, cell therapy or the development of medical or surgical devices, wherein fibrin or fibrinogen-containing supports are used.

Using supports for injection as for example collagen-based supports (collagen micro- or nanoparticles associated or not with other components which promote their polymerization or their association with a cell population modified to secrete factors or a particular activity such as for example an enzymatic activity aiming at cause the polymerization of collagen) or fibrin for injection that has been modified or not with adhesion molecules (a fibrin- or collagen-based gel with fibrinogen or fibrin having been modified with adhesion moieties) associated or not with cells could be used for promoting the fixation of the contractile tissue to the myocardium or for example to prepare or to contribute to prepare the site to which the transfer of the contractile patch will be performed by pre-vascularizing it for example. Cell therapies could improve the results obtained with the simple use of a contractile patch. The supports for injection could be injected into a tissue, into a support, into a device used in cardiothoracic and vascular applications, into a vessel or combinations thereof. Cells may be associated therewith previously, simultaneously or secondarily or combinations thereof. All the different types of cells are not necessarily present in the support at the same time. The support for injection may be used independently from the patch.

In some embodiments, the scaffold could be associated with a device which would aim at preventing ventricular remodeling or dilatation such as nets for example or a device which would aim at treating myocardial dysfunctions. These devices could surround part of or the whole heart. This device could be sometimes essentially composed of the contractile matrix. The application of an external scaffold could be associated with the injection of cells into the myocardium. These cells could be injected into a 3D-scaffold modified with adhesion molecules such as a RGD moiety.

To help revascularize these supports, some chemokines which promote the stem cell recruitment could be used like SDF1, SCF, TGF-alpha, FGF, etc. Agents aiming at mobilizing stem cells of the patient could also be used to help revascularize the implant.

We are conducting an international multicenter human trial by comparing the simple intra-myocardial injection of hematopoietic bone marrow cells into infarcted areas with the same injection of cells but this time associated with a collagen matrix application cellularized with marrow cells. This matrix at that time is not modified with adhesion peptides. (cf. Etude MAGNUM). We recently have demonstrated the interest of using such cellularized collagen matrix deposited onto the myocardium as compared to the simple injection of cells. (cf. J C Chachques, J G Trainini, J. Mouras, O. Schussler. Myocardial assistance by grafting a new bioartificial upgraded myocardium ( MAGNUM trial ): Preliminary results AATS (2006); J C. Chachques, J C. Traini, O. Schussler. Myocardial Assistance by Grafting a new bioartificial upgraded myocardium ( MAGNUM trial ): Clinical feasibility AHA (2006)). The development of collagen matrices that have been modified according to our proposal should markedly further improve the results expected in the near future.

It is an object of the present invention to improve the cell therapy in the medical field and in thoracic and cardiovascular surgery by using collagen scaffolds modified with adhesion molecules having, as a main application, the preparation of a contractile heart tissue. In addition to the cardiovascular and thoracic applications and, in a more general manner, such a support could be used for preparing a tissue that is spontaneously contractile or that becomes contractile upon electrostimulation. Such a tissue could be interesting for making a smooth muscle tissue or a skeletal tissue as to provide for example sphincters, vesical muscle, etc.

To be mentioned as main uses are the use of such supports in tissue engineering with the production of replacement tissue, reconstruction tissue, patch, tissue regeneration, healing acceleration, dehiscence prevention, desunion, air and/or liquid tightness, with amongst other things the production of myocardial tissues and/or valvular tissues (including valves, subvalvular apparatus and flush chamber), tracheobronchial and pulmonary tissues, vascular tissues, parietal and pericardial reconstruction tissues. Also included is the use of this type of support for cell therapy with the possibility for such support to be injected into a tissue, into a vascular or a bronchial lumen, into another support or medical or surgical device used in thoracic or cardiovascular surgery. Possibility to use this support for making a biological "pacemaker" by associating with cells having an intrinsic rhythmic activity such as dissociated atrial cardiac myocytes (nodal cells including sinus cells) of embryonal, fetal or adult origin or cells transformed having a rhythmic activity implanted into a biodegradable, pro-angiogenic matrix and intended to be implanted into heart. The association with adhesion peptides will retain the cell in the same place, will promote its survival, the interaction between cells with a better synchronization between each other and a better integration with the surrounding tissue.

This could lead to a method dedicated to heart tissue engineering by using a population of cells which would have or could develop contractile potentialities during their differentiation. Seeding of the cells within the cell matrix scaffold. Possibility of exposing the cell to one or more agents selected for promoting the cell differentiation, where the exposure step may be conducted prior to or after the implantation step into the matrix or both. The possibility of associating other types of cells such as cells belonging to the endothelial line. As for the contractile cells, the support will enable their survival, their differentiation. The present invention provides a means for making cardiac constructions in the absence of gel such as MATRIGEL™ (Becton-Dickinson) which is extracted from a tumor and reduces the nutrient diffusion thus leading to the production of thinner tissues. In addition, the terminal differentiation of the contractile cells does not necessarily require the use of chronic electrostimulation, the use of bioreactors, and the use of high doses of strongly immunogenic xenogeneic serum. Cell cultures may also be obtained on 2D-supports containing either fibrin or fibrinogen or collagen or any combination thereof, where at least one of these components is modified by the fixation of adhesion molecules. The adhesion of the cells to this support could be controlled. Cultures on fibrin-based based supports are currently under development[115]. Different layers of cells could be stacked so as to obtain thicker tissues[114]. Endothelial cells could be associated so as to promote angiogenesis. These supports could be applied onto heart by using systems such as collagen membranes to facilitate this application.

The construction may be formed in vitro for many weeks and can then be directly implanted into myocardium as a contractile insert or inside the myocardium aiming at replacing for example part of or the whole myocardial tissue. Alternatively the construction could be implanted in vivo in an ectopic site to promote the differentiation of the cells and their neovascularization. Such locations could be for example well-vascularized ectopic sites such as the peritoneal and pleural cavity, omentum, skeletal muscle electrostimulated or not, pleural cavity, pericardium, wall. The myocardium internal geometry could be provided by surrounding the tissue in situ with preferably non-adherent and non-resorbable structures such as silicone prostheses or any other synthetic polymer. These structures could be structures with variable geometry and could conform to a portion of the ventricular cavity. This device could be inflatable. The volume variations of such device could represent a means for applying some mechanical stress on myocardial tissue which is under development. Other stimuli such as a chronic electric stimulus could also be applied. A plurality of tissue layers could be successively stacked for making a thicker tissue during a first intervention or during a series of interventions. The vascularized construction may then be secondarily applied onto heart as a free graft or a pedicled graft, but it is also possible to replace part of or the whole thickness of the myocardium. The cellularized scaffold may be fixed to heart by using for example collagen or fibrin gels. These approaches may also use a cell therapy associated or not to a 3D-scaffold that has been modified or not with adhesion peptides. The ventricular patch may be a portion of or be associated with a heart contention device aiming at avoiding any cardiac dilatation, promoting a remodeling, improving the myocardial contractility, regenerating or treating myocardial conditions. The association of the myocardial contention device with a support intended to be cellularized provides a biological heart assistance. It is also possible to conceive a net which surrounds the heart and which could be cellularized. Using a contractile patch as an aortic prosthesis or applied to the native aorta that would be synchronized or not with the heart rate is an alternative way to provide a biological heart assistance.

Collagen matrices could also be used for cell therapy. The cells may be associated with supports functionalized with adhesion molecules and cross-linked in vitro or in vivo. In other situations, cells may be injected. Various forms of supports may then be used such as gels, hydrogels formed from nanoparticles of collagen, microspheres of collagen associated with organic or inorganic nanoparticles, collagen associated with organic or inorganic nanoparticles, etc. The present invention suggests to improve the biofunctionality of scaffolds containing fibrin alone or associated with collagen for example, by modifying fibrinogen, fibrin and/or collagen with the adhesion molecule fixation as proposed herein. Associating a RGD moiety during the polymerization of fibrin glue has been proposed for the injection of cells into the heart. But, in this case, the adhesion molecules are non-fixed adhesion molecules which functionality may be improved (U.S. Patent No. 2005/2,761,631). The adhesion molecules may be associated with fibrinogen or with collagen in vitro. The enzyme associated at the time of injection, generally thrombin in the presence of calcium, induces the conversion of fibrinogen to fibrin and the formation of the three-dimensional support. Such fibrin/fibrinogen/collagen scaffold optionally associated with other components could be used for tissue engineering, cell therapy or for making various medical and/or surgical devices not only in the cardiovascular field.

The surgical and medical devices of the thoracic and cardiovascular field which would be advantageously improved include a viable valve, stented or not stented, prepared from a collagen- or fibrin/fibrinogen-containing support modified and cellularized with autologous or non-autologous cells (i.e. supports that are different from those proposed such as synthetic matrices (U.S. patents No. 2006/0,253,192, 2006/0,246,584), resorptive valvular rings or viable rings with possibility of remodeling, myocardial-containment net which contains collagen or which is associated with a collagen-containing support or external biological assistance aiming at improving contraction and/or regeneration and/or remodeling and/or myocardial containment and/or at treating myocardial conditions or a pathological myocardium and/or at maintaining a cellularized support, biological glues, hemocompatibility membranes, poorly thrombogenic, cardiac valvular bioprostheses, tube valves, production of prostheses, endoprostheses and vascular stents, vascular substitutes with for example collagen scaffolds modified so as to obtain poorly thrombogenic grafts (vascular grafts including coronary grafts), preparation of vascular grafts that are spontaneously contractile or become contractile upon electrostimulation, where such grafts could be used for heart assistance, coronary and endosinus stents (drug eluted stents, resorptive stents, cellularized stents) (association of cyclic RGD to the metal component of the drug eluted stent already proposed in the U.S. patent No. 2005/0,123,582), modification of the collagen content in endobronchial coils or by-pass with also the possibility of associating cells of interest therewith, tracheobronchial prostheses and endotracheal or endobronchial stent, supports for releasing a bioactive agent.

The biocompatibility of collagen scaffolds typically reconstituted from collagen fibers is greatly improved if after the genipin-mediated cross-linking they are partially covered with proteoglycans according to the traditional methods already used for fixing tissues with genipin. When traditionally fixing collagen scaffolds (tissues, reconstituted supports or collagen-containing devices) with glutararaldehyde the biocompatibility is improved thanks to a subsequent proteoglycan fixation through a protein coupling reactant such as soluble carbodiimide, optionally followed with a reduction with sodium borohydride or sodium cyanoborohydride. The collagen component of these supports may be advantageously functionalized with adhesion molecules.

The collagen scaffolds modified according to the present invention may in addition find an important application for cell therapy in muscles, the engineering of tissues contracting spontaneously or under stimulation (smooth, skeletal or cardiac muscles), general cell therapy using contractile potential cells which may be optionally genetically modified so as to release bioactive agents for example.

It is also possible to use the modified or not, fibrin/fibrinogen supports with or without collagen for cell therapy, tissue engineering and for making medical and/or surgical devices in general.

1. Yasuda, T. et al. Quantitative analysis of survival of transplanted smooth muscle cells with real-time polymerase chain reaction. *J Thorac Cardiovasc Surg* 129, 904-11 (2005).
2. Whittaker, P., Muller-Ehmsen, J., Dow, J. S., Kedes, L. H. & Kloner, R. A. Development of abnormal tissue architecture in transplanted neonatal rat myocytes. *Ann Thorac Surg* 75, 1450-6 (2003).
3. Mangi, A. A. et al. Mesenchymal stem cells modified with Akt prevent remodeling and restore performance of infarcted hearts. *Nat Med* 9, 1195-201 (2003).
4. Leor, J., Amsalem, Y. & Cohen, S. Cells, scaffolds, and molecules for myocardial tissue engineering. *Pharmacol Ther* 105, 151-63 (2005).

5. Zimmermann, W. H., Melnychenko, I. & Eschenhagen, T. Engineered heart tissue for regeneration of diseased hearts. *Biomaterials* 25, 1639-47 (2004).
6. Eschenhagen, T. & Zimmermann, W. H. Engineering myocardial tissue. *Circ Res* 97, 1220-31 (2005).
7. Nugent, H. M. & Edelman, E. R. Tissue engineering therapy for cardiovascular disease. *Circ Res* 92, 1068-78 (2003).
8. Shachar, M. & Cohen, S. Cardiac tissue engineering, ex-vivo: design principles in biomaterials and bioreactors. *Heart Fail Rev* 8, 271-6 (2003).
9. Suuronen, E. J. et al. Tissue-engineered injectable collagen-based matrices for improved cell delivery and vascularization of ischemic tissue using CD133+ progenitors expanded from the peripheral blood. *Circulation* 114, I138-44 (2006).
10. Qian, H., Yang, Y., Huang, J., Dou, K. & Yang, G. Cellular cardiomyoplasty by catheter-based infusion of stem cells in clinical settings. *Transpl Immunol* 16, 135-47 (2006).
11. Kumaran, V., Joseph, B., Benten, D. & Gupta, S. Integrin and extracellular matrix interactions regulate engraftment of transplanted hepatocytes in the rat liver. *Gastroenterology* 129, 1643-53 (2005).
12. MacDonald, R. A., Laurenzi, B. F., Viswanathan, G., Ajayan, P. M. & Stegemann, J. P. Collagen-carbon nanotube composite materials as scaffolds in tissue engineering. *J Biomed Mater Res A* 74, 489-96 (2005).
13. Griffith, L. G. & Swartz, M. A. Capturing complex 3D tissue physiology in vitro. *Nat Rev Mol Cell Biol* 7, 211-24 (2006).
14. Vogel, V. & Sheetz, M. Local force and geometry sensing regulate cell functions. *Nat Rev Mol Cell Biol* 7, 265-75 (2006).
15. Badylak, S. F. Xenogeneic extracellular matrix as a scaffold for tissue reconstruction. *Transpl Immunol* 12, 367-77 (2004).
16. Samarel, A. M. Costameres, focal adhesions, and cardiomyocyte mechanotransduction. *Am J Physiol Heart Circ Physiol* 289, H2291-301 (2005).
17. Kuppuswamy, D. Importance of integrin signaling in myocyte growth and survival. *Circ Res* 90, 1240-2 (2002).
18. Meredith, J. & Schwartz, M. *Integrins, adhesion and apoptosis,* 146-150 (1997).
19. Walker, J. L., Fournier, A. K. & Assoian, R. K. Regulation of growth factor signaling and cell cycle progression by cell adhesion and adhesion-dependent changes in cellular tension. *Cytokine Growth Factor Rev* 16, 395-405 (2005).
20. Chen, S. S., Fitzgerald, W., Zimmerberg, J., Kleinman, H. K. & Margolis, L. Cell-cell and cell-extracellular matrix interactions regulate embryonic stem cell differentiation. *Stem Cells* 25, 553-61 (2007).
21. Liu, W. F. & Chen, S. C. Engineering biomaterials to control cell function. *Materials Today* 8, 28-35 (2005).
22. Hersel, U., Dahmen, C. & Kessler, H. RGD modified polymers: biomaterials for stimulated cell adhesion and beyond. *Biomaterials* 24, 4385-415 (2003).
23. Beer, J. H., Springer, K. T. & Coller, B. S. Immobilized Arg-Gly-Asp (RGD) peptides of varying lengths as structural probes of the platelet glycoprotein IIb/IIIa receptor. *Blood* 79, 117-28 (1992).
24. Craig, W. S., Cheng, S., Mullen, D. G., Blevitt, J. & Pierschbacher, M. D. Concept and progress in the development of RGD-containing peptide pharmaceuticals. *Biopolymers* 37, 157-75 (1995).
25. Katsumi, A., Orr, A. W., Tzima, E. & Schwartz, M. A. Integrins in mechanotransduction. *J Biol Chem* 279, 12001-4 (2004).
26. Reinhart-King, C. A., Dembo, M. & Hammer, D. A. The dynamics and mechanics of endothelial cell spreading. *Biophys J* 89, 676-89 (2005).
27. Simon, A. & Durrieu, M. C. Strategies and results of atomic force microscopy in the study of cellular adhesion. *Micron* 37, 1-13 (2006).
28. Engler, A. J. et al. Myotubes differentiate optimally on substrates with tissue-like stiffness: pathological implications for soft or stiff microenvironments. *J Cell Biol* 166, 877-87 (2004).
29. Deroanne, C. F., Lapiere, C. M. & Nusgens, B. V. In vitro tubulogenesis of endothelial cells by relaxation of the coupling extracellular matrix-cytoskeleton. *Cardiovasc Res* 49, 647-58 (2001).
30. Leor, J. & Cohen, S. Myocardial tissue engineering: creating a muscle patch for a wounded heart. *Ann N Y Acad Sci* 1015, 312-9 (2004).
31. Davis, M. E. et al. Injectable self-assembling peptide nanofibers create intramyocardial microenvironments for endothelial cells. *Circulation* 111, 442-50 (2005).
32. Narmoneva, D. A., Vukmirovic, R., Davis, M. E., Kamm, R. D. & Lee, R. T. Endothelial cells promote cardiac myocyte survival and spatial reorganization: implications for cardiac regeneration. *Circulation* 110, 962-8 (2004).
33. Weadock, K. S., Miller, E. J., Keuffel, E. L. & Dunn, M. G. Effect of physical crosslinking methods on collagen-fiber durability in proteolytic solutions. *J Biomed Mater Res* 32, 221-6 (1996).
34. Cornwell, K. G., Lei, P., Andreadis, S. T. & Pins, G. D. Crosslinking of discrete self-assembled collagen threads: Effects on mechanical strength and cell-matrix interactions. *J Biomed Mater Res A* 80, 362-71 (2007).
35. Kannan, R. Y., Salacinski, H. J., Sales, K., Butler, P. & Seifalian, A. M. The roles of tissue engineering and vascularisation in the development of micro-vascular networks: a review. *Biomaterials* 26, 1857-75 (2005).
36. Ilan, N., Mahooti, S. & Madri, J. A. Distinct signal transduction pathways are utilized during the tube formation and survival phases of in vitro angiogenesis. *J Cell Sci* 111 (Pt 24), 3621-31 (1998).
37. Satake, S., Kuzuya, M., Ramos, M. A., Kanda, S. & Iguchi, A. Angiogenic stimuli are essential for survival of vascular endothelial cells in three-dimensional collagen lattice. *Biochem Biophys Res Commun* 244, 642-6 (1998).
38. Ranta, V., Mikkola, T., Ylikorkala, O., Viinikka, L. & Orpana, A. Reduced viability of human vascular endothelial cells cultured on Matrigel. *J Cell Physiol* 176, 92-8 (1998).
39. Goto, F., Goto, K., Weindel, K. & Folkman, J. Synergistic effects of vascular endothelial growth factor and basic fibroblast growth factor on the proliferation and cord formation of bovine capillary endothelial cells within collagen gels [see comments]. *Laboratory Investigation* 69, 508-17 (1993).
40. Radisic, M. et al. Functional assembly of engineered myocardium by electrical stimulation of cardiac myocytes cultured on scaffolds. *Proc Natl Acad Sci USA* 101, 18129-34 (2004).
41. Radisic, M. et al. Medium perfusion enables engineering of compact and contractile cardiac tissue. *Am J Physiol Heart Circ Physiol* 286, H507-16 (2004).
42. Souren, J. E., Peters, R. C. & Van Wijk, R. Collagen gels populated with rat neonatal heart cells can be used for optical recording of rhythmic contractions which also show ECG-like potentials. *Experientia* 50, 712-6 (1994).

43. Souren, J. E., Schneijdenberg, C., Verkleij, A. J. & Van Wijk, R. Factors controlling the rhythmic contraction of collagen gels by neonatal heart cells. *In Vitro Cell Dev Biol* 28A, 199-204 (1992).
44. Zimmermann, W. H. et al. Three-dimensional engineered heart tissue from neonatal rat cardiac myocytes. *Biotechnol Bioeng* 68, 106-14 (2000).
45. Zimmermann, W. H. et al. Engineered heart tissue grafts improve systolic and diastolic function in infarcted rat hearts. *Nat Med* 12, 452-8 (2006).
46. Eschenhagen, T., Didie, M., Heubach, J., Ravens, U. & Zimmermann, W. H. Cardiac tissue engineering. *Transpl Immunol* 9, 315-21 (2002).
47. Zimmermann, W. H. et al. Cardiac grafting of engineered heart tissue in syngenic rats. *Circulation* 106, I151-7 (2002).
48. von Wnuck Lipinski, K. et al. Integrin-mediated transcriptional activation of inhibitor of apoptosis proteins protects smooth muscle cells against apoptosis induced by degraded collagen. *Circ Res* 98, 1490-7 (2006).
49. Meinel, L. et al. Engineering cartilage-like tissue using human mesenchymal stem cells and silk protein scaffolds. *Biotechnol Bioeng* 88, 379-91 (2004).
50. Coyle, C. H., Mendralla, S., Lanasa, S. & Kader, K. N. Endothelial Cell Seeding onto Various Biomaterials Causes Superoxide-induced Cell Death. *J Biomater Appl* (2006).
51. Grzesiak, J. J., Pierschbacher, M. D., Amodeo, M. F., Malaney, T. I. & Glass, J. R. Enhancement of cell interactions with collagen/glycosaminoglycan matrices by RGD derivatization. *Biomaterials* 18, 1625-32 (1997).
52. Dagalakis, N., Flink, J., Stasikelis, P., Burke, J. F. & Yannas, I. V. Design of an artificial skin. Part III. Control of pore structure. *J Biomed Mater Res* 14, 511-28 (1980).
53. Yannas, I. V., Lee, E., Orgill, D. P., Skrabut, E. M. & Murphy, G. F. Synthesis and characterization of a model extracellular matrix that induces partial regeneration of adult mammalian skin. *Proc Natl Acad Sci USA* 86, 933-7 (1989).
54. Suuronen, E. J. et al. Innervated human corneal equivalents as in vitro models for nerve-target cell interactions. *Faseb J* 18, 170-2 (2004).
55. Kofidis, T. et al. Clinically established hemostatic scaffold (tissue fleece) as biomatrix in tissue- and organ-engineering research. *Tissue Eng* 9, 517-23 (2003).
56. Park, H., Radisic, M., Lim, J. O., Chang, B. H. & Vunjak-Novakovic, G. A novel composite scaffold for cardiac tissue engineering. *In Vitro Cell Dev Biol Anim* 41, 188-96 (2005).
57. Chen, R. N., Ho, H. O. & Sheu, M. T. Characterization of collagen matrices crosslinked using microbial transglutaminase. *Biomaterials* 26, 4229-35 (2005).
58. Goissis, G. et al. Biocompatibility studies of anionic collagen membranes with different degree of glutaraldehyde cross-linking. *Biomaterials* 20, 27-34 (1999).
59. Park, S. N., Park, J. C., Kim, H. O., Song, M. J. & Suh, H. Characterization of porous collagen/hyaluronic acid scaffold modified by 1-ethyl-3-(3-dimethylaminopropyl)carbodiimide cross-linking. *Biomaterials* 23, 1205-12 (2002).
60. Zandonella, C. Tissue engineering: The beat goes on. *Nature* 421, 884-6 (2003).
61. Jockenhoevel, S. et al. Fibrin gel—advantages of a new scaffold in cardiovascular tissue engineering. *Eur J Cardiothorac Surg* 19, 424-30 (2001).
62. Christman, K. L., Fok, H. H., Sievers, R. E., Fang, Q. & Lee, R. J. Fibrin glue alone and skeletal myoblasts in a fibrin scaffold preserve cardiac function after myocardial infarction. *Tissue Eng* 10, 403-9 (2004).
63. Christman, K. L. et al. Injectable fibrin scaffold improves cell transplant survival, reduces infarct expansion, and induces neovasculature formation in ischemic myocardium. *J Am Coll Cardiol* 44, 654-60 (2004).
64. Mol, A. et al. Fibrin as a cell carrier in cardiovascular tissue engineering applications. *Biomaterials* 26, 3113-21 (2005).
65. Rowe, S. L., Lee, S. & Stegemann, J. P. Influence of thrombin concentration on the mechanical and morphological properties of cell-seeded fibrin hydrogels. *Acta Biomater* 3, 59-67 (2007).
66. Liu, W. et al. Fibrin fibers have extraordinary extensibility and elasticity. *Science* 313, 634 (2006).
67. Boublik, J. et al. Mechanical properties and remodeling of hybrid cardiac constructs made from heart cells, fibrin, and biodegradable, elastomeric knitted fabric. *Tissue Eng* 11, 1122-32 (2005).
68. Beier, J. P. et al. Tissue engineering of injectable muscle: three-dimensional myoblast-fibrin injection in the syngeneic rat animal model. *Plast Reconstr Surg* 118, 1113-21; discussion 1122-4 (2006).
69. Williams, C., Johnson, S. L., Robinson, P. S. & Tranquillo, R. T. Cell sourcing and culture conditions for fibrin-based valve constructs. *Tissue Eng* 12, 1489-502 (2006).
70. McKenna, C. J. et al. Fibrin-film stenting in a porcine coronary injury model: efficacy and safety compared with uncoated stents. *J Am Coll Cardiol* 31, 1434-8 (1998).
71. Gutierrez San Roman, C. et al. Long-term assessment of the treatment of recurrent tracheoesophageal fistula with fibrin glue associated with diathermy. *J Pediatr Surg* 41, 1870-3 (2006).
72. Schense, J. C., Bloch, J., Aebischer, P. & Hubbell, J. A. Enzymatic incorporation of bioactive peptides into fibrin matrices enhances neurite extension. *Nat Biotechnol* 18, 415-9 (2000).
73. Hall, H., Baechi, T. & Hubbell, J. A. Molecular properties of fibrin-based matrices for promotion of angiogenesis in vitro. *Microvasc Res* 62, 315-26 (2001).
74. Korff, T. & Augustin, H. G. Tensional forces in fibrillar extracellular matrices control directional capillary sprouting. *J Cell Sci* 112 (Pt 19), 3249-58 (1999).
75. Eyrich, D. et al. Long-term stable fibrin gels for cartilage engineering. *Biomaterials* 28, 55-65 (2007).
76. Cummings, C. L., Gawlitta, D., Nerem, R. M. & Stegemann, J. P. Properties of engineered vascular constructs made from collagen, fibrin, and collagen-fibrin mixtures. *Biomaterials* 25, 3699-706 (2004).
77. Rowe, S. L. & Stegemann, J. P. Interpenetrating collagen-fibrin composite matrices with varying protein contents and ratios. *Biomacromolecules* 7, 2942-8 (2006).
78. Sarin, V., Gaffin, R. D., Meininger, G. A. & Muthuchamy, M. Arginine-glycine-aspartic acid (RGD)-containing peptides inhibit the force production of mouse papillary muscle bundles via alpha 5 beta 1 integrin. *J Physiol* 564, 603-17 (2005).
79. Balasubramanian, S. & Kuppuswamy, D. RGD-containing peptides activate S6K1 through beta3 integrin in adult cardiac muscle cells. *J Biol Chem* 278, 42214-24 (2003).
80. Boateng, S. Y. et al. RGD and YIGSR synthetic peptides facilitate cellular adhesion identical to that of laminin and fibronectin but alter the physiology of neonatal cardiac myocytes. *Am J Physiol Cell Physiol* 288, C30-8 (2005).
81. Blindt, R. et al. A novel drug-eluting stent coated with an integrin-binding cyclic Arg-Gly-Asp peptide inhibits 81. neointimal hyperplasia by recruiting endothelial progenitor cells. *J Am Coll Cardiol* 47, 1786-95 (2006).
82. Myles, J. L., Burgess, B. T. & Dickinson, R. B. Modification of the adhesive properties of collagen by covalent grafting with RGD peptides. *J Biomater Sci Polym* Ed 11, 69-86 (2000).
83. Lindberg, K. & Badylak, S. F. Porcine small intestinal submucosa (SIS): a bioscaffold supporting in vitro primary human epidermal cell differentiation and synthesis of basement membrane proteins. *Burns* 27, 254-66 (2001).
84. Badylak, S. F., Record, R., Lindberg, K., Hodde, J. & Park, K. Small intestinal submucosa: a substrate for in vitro cell growth. *J Biomater Sci Polym* Ed 9, 863-78 (1998).
85. Pierschbacher, M. D. & Ruoslahti, E. Cell attachment activity of fibronectin can be duplicated by small synthetic fragments of the molecule. *Nature* 309, 30-3 (1984).
86. Pfaff, M., McLane, M. A., Beviglia, L., Niewiarowski, S. & Timpl, R. Comparison of disintegrins with limited variation in the RGD loop in their binding to purified integrins alpha IIb beta 3, alpha V beta 3 and alpha 5 beta 1 and in cell adhesion inhibition. Cell Adhes Commun 2, 491-501 (1994).
87. Iwamoto, Y. et al. YIGSR, a synthetic laminin pentapeptide, inhibits experimental metastasis formation. *Science* 238, 1132-4 (1987).
88. Tashiro, K. et al. A synthetic peptide containing the IKVAV sequence from the A chain of laminin mediates cell attachment, migration, and neurite outgrowth. J Biol Chem 264, 16174-82 (1989).
89. Liesi, P., Narvanen, A., Soos, J., Sariola, H. & Snounou, G. Identification of a neurite outgrowth-promoting domain of laminin using synthetic peptides. FEBS Lett 244, 141-8 (1989).
90. Massia, S. P. & Hubbell, J. A. Vascular endothelial cell adhesion and spreading promoted by the peptide REDV of the IIICS region of plasma fibronectin is mediated by integrin alpha 4 beta 1. J Biol Chem 267, 14019-26 (1992).
91. Altroff, H. et al. The eighth FIII domain of human fibronectin promotes integrin alpha5beta1 binding via stabilization of the ninth FIII domain. J Biol Chem 276, 38885-92 (2001).
92. Wong, J. Y., Weng, Z., Moll, S., Kim, S. & Brown, C. T. Identification and validation of a novel cell-recognition site (KNEED) on the 8th type III domain of fibronectin. Biomaterials 23, 3865-70 (2002).
93. Dee, K. C., Andersen, T. T. & Bizios, R. Design and function of novel osteoblast -adhesive peptides for chemical modification of biomaterials. J Biomed Mater Res 40, 371-7 (1998).
94. Rezania, A. & Healy, K. E. Biomimetic peptide surfaces that regulate adhesion, spreading, cytoskeletal organization, and mineralization of the matrix deposited by osteoblast-like cells. Biotechnol Prog 15, 19-32 (1999).
95. Rezania, A. & Healy, K. E. Integrin subunits responsible for adhesion of human osteoblast-like cells to biomimetic peptide surfaces. J Orthop Res 17, 615-23 (1999).
96. Mann, B. K. & West, J. L. Cell adhesion peptides alter smooth muscle cell adhesion, proliferation, migration, and matrix protein synthesis on modified surfaces and in polymer scaffolds. *J Biomed Mater Res* 60, 86-93 (2002).
97. Emsley, J., Knight, C. G., Farndale, R. W., Barnes, M. J. & Liddington, R. C. Structural basis of collagen recognition by integrin alpha2beta1. Cell 101, 47-56 (2000).
98. Lee, W. K. et al. Improved calcification resistance and biocompatibility of tissue patch grafted with sulfonated PEO or heparin after glutaraldehyde fixation. J Biomed Mater Res 58, 27-35 (2001).
99. Chang, Y., Liang, H. C., Wei, H. J., Chu, C. P. & Sung, H. W. Tissue regeneration patterns in acellular bovine pericardia implanted in a canine model as a vascular patch. J Biomed Mater Res A 69, 323-33 (2004).
100. Chang, Y., Tsai, C. C., Liang, H. C. & Sung, H. W. In vivo evaluation of cellular and acellular bovine pericardia fixed with a naturally occurring crosslinking agent (genipin). Biomaterials 23, 2447-57 (2002).
101. Levenberg, S. et al. Engineering vascularized skeletal muscle tissue. Nat Biotechnol 23, 879-84 (2005).
102. Radisic, M. et al. High-density seeding of myocyte cells for cardiac tissue engineering. Biotechnol Bioeng 82, 403-14 (2003).
103. Coirault, C., Chemla, D., Suard, I., Pourny, J. C. & Lecarpentier, Y. Sarcomere relaxation in hamster diaphragm muscle. J Appl Physiol 81, 858-65 (1996).
104. Lecarpentier, Y. et al. Mechanics, energetics, and cross-bridge kinetics of rabbit diaphragm during congestive heart failure. Faseb J 12, 981-9 (1998).
105. Lecarpentier, Y. et al. Real-time kinetics of sarcomere relaxation by laser diffraction. Circ Res 56, 331-9 (1985).
106. Black, A. F., Berthod, F., L'heureux, N., Germain, L. & Auger, F. A. In vitro reconstruction of a human capillary-like network in a tissue-engineered skin equivalent. Faseb Journal 12, 1331-40 (1998).
107. Baatout, S. Endothelial differentiation using Matrigel (review). Anticancer Research 17, 451-5 (1997).
108. Montesano, R., Pepper, M. S. & Orci, L. Paracrine induction of angiogenesis in vitro by Swiss 3T3 fibroblasts. *Journal of Cell Science* 105 (Pt 4), 1013-24 (1993).
109. De Coppi, P. et al. Angiogenic gene-modified muscle cells for enhancement of tissue formation. Tissue Eng 11, 1034-44 (2005).
110. Arbiser, J. L. et al. Oncogenic H-ras stimulates tumor angiogenesis by two distinct pathways. proceedings of the national academy of sciences of the united states of america 94, 861-6 (1997).
111. Cherqui, S. et al. Isolation and angiogenesis by endothelial progenitors in the fetal liver. *Stem Cells* 24, 44-54 (2006).
112. Hildbrand, P. et al. The role of angiopoietins in the development of endothelial cells from cord blood CD34+ progenitors. *Blood* 104, 2010-9 (2004).
113. Crisa, L. et al. Human cord blood progenitors sustain thymic T-cell development and a novel form of angiogenesis. Blood 94, 3928-40 (1999).
114. Shimizu, T. et al. Polysurgery of cell sheet grafts overcomes diffusion limits to produce thick, vascularized myocardial tissues. Faseb J 20, 708-10 (2006).
115. Furuta, A. et al. Pulsatile cardiac tissue grafts using a novel three-dimensional cell sheet manipulation technique functionally integrates with the host heart, in vivo. *Circ Res* 98, 705-12 (2006).

The invention claimed is:

1. A method for making a solid three-dimensional scaffold for cell therapy, tissue engineering and medico-surgical devices in the thoracic and surgical field, comprising:
providing a scaffold support comprising a cross-linked collagen matrix, the collagen matrix being a collagen sponge and the collagen being purified from collagen-containing tissue;
further crosslinking the collagen matrix; and
modifying the scaffold support by covalently binding adhesion molecules to the collagen, wherein the adhesion molecules are RGD-containing peptides, said binding comprising covalently and uni-directionally binding primary amine groups present in the adhesion molecules to primary amine groups present in the collagen utilizing the heterobifunctional coupling reagent sulfosuccinimidyl 6-(3'-[2-pyridyldithio]-propionamido)hexanoate (Sulfo-LC-SPDP), said binding being performed by reacting the collagen with Sulfo-LC-SPDP, wherein the Sulfo-LC-SPDP covalently binds to a primary amine group of the collagen;

reacting the adhesion molecules with Sulfo-LC-SPDP, wherein the Sulfo-LC-SPDP covalently binds to a primary amine group of the adhesion molecule; and reacting the Sulfo-LC-SPDP covalently bound to the collagen with the Sulfo-LC-SPDP covalently bound to the adhesion molecule, the Sulfo-LC-SPDP coupling reagents covalently binding together to form a disulfide bond, wherein the RGD-modified collagen matrix allows survival and differentiation of implanted contractile or potential contractile cells and forms a spontaneously contractile three dimensional scaffold.

2. The method according to claim 1, further comprising incorporating the three-dimensional scaffold in to a medico-surgical device in the thoracic and surgical field, wherein the device is selected from the group consisting of: a biological pacemaker, a cellularized coronary stent for improving local angiogenesis and allowing a biological by-pass, a biological valvular ring that is adaptable and contractile, a small-sized coronary graft, a viable valve, a tissue patch, a valvular cordage, a guiding device for securing surgical procedures, a device for ensuring tightness towards liquids or air, a papillary muscle for treating post-infarct pillar necrosis, a vascular prosthesis, a contractile vascular prosthesis that can be electrically stimulated so as to provide an internal biological assistance, a device for treating myocardial conditions that combines a system for monitoring remodeling or limiting ventricular distension through containment and a system for improving myocardial contractility, a device for releasing an active agent, a biological glue, a device for treating pulmonary emphysema and recolonizing and reconstituting the pathological pulmonary parenchyma by associating cells with a three-dimensional scaffold, a device for improving permeability of a by-pass and collagen bronchial coil, an active agent-releasing endobronchial device for use in tumor pathology or for treating respiratory system dysfunctions, and a scaffold for cell therapy and tissue engineering in the thoracic and cardiovascular field.

3. The method according to claim 1, wherein the contractile or potential contractile cells comprise smooth or skeletal muscles or contractile tissues.

4. The method according to claim 1, wherein the collagen matrix is cross-linked with glutaraldehyde and a Schiff base-reducing reactant, or with genipin.

5. The method according to claim 1, further comprising treating the scaffold with proteoglycans.

6. The method according to claim 1, further comprising implanting the three-dimensional scaffold with said contractile or potential contractile cells.

7. The method according to claim 1, wherein the three-dimensional scaffold is associated with one or more bioactive molecules.

8. The method according to claim 1, wherein the scaffold support has a pore size in a range of from 30 μm to 200 μm.

9. The method according to claim 1, wherein the collagen sponge is cross-linked by dehydrothermal crosslinking.

10. The method according to claim 9, wherein the collagen matrix is further cross-linked with glutaraldehyde and a Schiff base-reducing agent, or with genipin, before or after said covalently binding adhesion molecules to the collagen.

11. The method according to claim 1, further comprising in vitro implanting the collagen matrix with said contractile or potential contractile cells.

12. The method according to claim 11, further comprising colonization of the collagen matrix with the implanted contractile or potential contractile cells.

* * * * *